US009377388B2

(12) United States Patent
Walt et al.

(10) Patent No.: US 9,377,388 B2
(45) Date of Patent: *Jun. 28, 2016

(54) METHODS FOR DETECTING TARGET ANALYTES AND ENZYMATIC REACTIONS

(75) Inventors: David R. Walt, Boston, MA (US); Karri Lynn Michael-Ballard, Pflugerville, TX (US)

(73) Assignee: Trustees of Tufts College, Medford, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 13/108,713

(22) Filed: May 16, 2011

(65) Prior Publication Data
US 2011/0251105 A1 Oct. 13, 2011

Related U.S. Application Data

(63) Continuation of application No. 12/265,697, filed on Nov. 5, 2008, now abandoned, which is a continuation of application No. 10/920,637, filed on Aug. 17, 2004, now Pat. No. 7,622,294, which is a continuation-in-part of application No. 09/786,896, filed as application No. PCT/US99/20914 on Sep. 10, 1999, now abandoned, which is a continuation of application No. 09/151,877, filed on Sep. 11, 1998, now Pat. No. 6,327,410, which is a continuation-in-part of application No. 08/818,199, filed on Mar. 14, 1997, now Pat. No. 6,023,540, said application No. 10/920,637 is a continuation-in-part of application No. 09/840,012, filed on Apr. 20, 2001, now abandoned, which is a continuation of application No. 09/450,829, filed on Nov. 29, 1999, now Pat. No. 6,266,459, which is a continuation of application No.

(Continued)

(51) Int. Cl.
*C12Q 1/68* (2006.01)
*G01N 15/14* (2006.01)
*B01J 19/00* (2006.01)
*B82Y 30/00* (2011.01)
*G01N 21/64* (2006.01)
*G01N 33/543* (2006.01)
*C40B 40/06* (2006.01)
*C40B 40/10* (2006.01)
*G01N 35/00* (2006.01)

(52) U.S. Cl.
CPC ......... *G01N 15/1456* (2013.01); *B01J 19/0046* (2013.01); *B82Y 30/00* (2013.01); *G01N 21/6452* (2013.01); *G01N 33/543* (2013.01); *G01N 33/54313* (2013.01); *B01J 2219/005* (2013.01); *B01J 2219/0061* (2013.01); *B01J 2219/0074* (2013.01); *B01J 2219/00317* (2013.01); *B01J 2219/00466* (2013.01); *B01J 2219/00524* (2013.01); *B01J 2219/00585* (2013.01); *B01J 2219/00596* (2013.01); *B01J 2219/00605* (2013.01); *B01J 2219/00612* (2013.01); *B01J 2219/00621* (2013.01); *B01J 2219/00626* (2013.01); *B01J 2219/00637* (2013.01); *B01J 2219/00648* (2013.01); *B01J 2219/00659* (2013.01); *B01J 2219/00677* (2013.01); *B01J 2219/00704* (2013.01); *B01J 2219/00722* (2013.01); *B01J 2219/00725* (2013.01); *C12Q 1/6837* (2013.01); *C40B 40/06* (2013.01); *C40B 40/10* (2013.01); *G01N 2015/1438* (2013.01); *G01N 2021/6484* (2013.01); *G01N 2035/0097* (2013.01); *G01N 2201/0826* (2013.01)

(58) Field of Classification Search
None
See application file for complete search history.

(56) References Cited

U.S. PATENT DOCUMENTS 3,574,614 A  4/1971 Carreia
3,791,192 A  2/1974 Butler
(Continued)

FOREIGN PATENT DOCUMENTS

CA   1248873   12/1917
CA   1248873   1/1989
(Continued)

OTHER PUBLICATIONS

Campian, et al., "Colored and Fluorescent Solid Supports" *Innovation and Perspectives in Solid-Phase Synthesis*, Ed. E. Birmingham (Mayflower, London), pp. 469-472 (1994).
(Continued)

*Primary Examiner* — Ann Lam
(74) *Attorney, Agent, or Firm* — Knobbe, Martens, Olson & Bear LLP

(57) ABSTRACT

A microsphere-based analytic chemistry system and method for making the same is disclosed in which microspheres or particles carrying bioactive agents may be combined randomly or in ordered fashion and dispersed on a substrate to form an array while maintaining the ability to identify the location of bioactive agents and particles within the array using an optically interrogatable, optical signature encoding scheme. A wide variety of modified substrates may be employed which provide either discrete or non-discrete sites for accommodating the microspheres in either random or patterned distributions. The substrates may be constructed from a variety of materials to form either two-dimensional or three-dimensional configurations. In a preferred embodiment, a modified fiber optic bundle or array is employed as a substrate to produce a high density array. The disclosed system and method have utility for detecting target analytes and screening large libraries of bioactive agents.

12 Claims, 9 Drawing Sheets

Related U.S. Application Data

08/818,199, filed on Mar. 14, 1997, now Pat. No. 6,023,540, said application No. 10/920,637 is a continuation-in-part of application No. 09/925,292, filed on Aug. 8, 2001, now Pat. No. 6,859,570, which is a continuation of application No. 09/151,877, filed on Sep. 11, 1998, now Pat. No. 6,327,410, which is a continuation-in-part of application No. 08/818,199, filed on Mar. 14, 1997, now Pat. No. 6,023,540, said application No. 10/920,637 is a continuation-in-part of application No. 09/816,651, filed on Mar. 23, 2001, now abandoned, which is a continuation of application No. 09/450,829, filed on Nov. 29, 1999, now Pat. No. 6,266,459, which is a continuation of application No. 08/818,199, filed on Mar. 14, 1997, now Pat. No. 6,023,540.

(56) References Cited

U.S. PATENT DOCUMENTS

| | | | |
|---|---|---|---|
| 3,992,631 | A | 11/1976 | Harte |
| 3,998,525 | A | 12/1976 | Giglia |
| 4,018,635 | A | 4/1977 | Ryan et al. |
| 4,075,013 | A | 2/1978 | Ward et al. |
| 4,200,110 | A | 4/1980 | Peterson et al. |
| 4,456,513 | A | 6/1984 | Kawai et al. |
| 4,499,052 | A | 2/1985 | Fulwyer |
| 4,575,407 | A | 3/1986 | Diller |
| 4,591,550 | A | 5/1986 | Hafeman et al. |
| 4,647,544 | A | 3/1987 | Nicoli et al. |
| 4,665,020 | A | 5/1987 | Saunders |
| 4,675,283 | A | 6/1987 | Roninson |
| 4,682,895 | A | 7/1987 | Costello |
| 4,717,655 | A | 1/1988 | Fulwyler |
| 4,775,619 | A | 10/1988 | Urdea |
| 4,785,814 | A | 11/1988 | Kane |
| 4,791,310 | A | 12/1988 | Honig et al. |
| 4,822,746 | A | 4/1989 | Walt |
| 4,824,789 | A | 4/1989 | Yafuso et al. |
| 4,907,037 | A | 3/1990 | Biosde et al. |
| 4,971,903 | A | 11/1990 | Hyman |
| 4,994,373 | A | 2/1991 | Stavrianopoulos et al. |
| 4,999,306 | A | 3/1991 | Yafuso et al. |
| 5,002,867 | A | 3/1991 | Macevicz |
| 5,028,545 | A | 7/1991 | Soini |
| 5,105,305 | A | 4/1992 | Betzig et al. |
| 5,114,864 | A | 5/1992 | Walt |
| 5,132,097 | A | 7/1992 | Van Deusen et al. |
| 5,132,242 | A | 7/1992 | Cheung |
| 5,143,853 | A | 9/1992 | Walt |
| 5,194,300 | A | 3/1993 | Cheung |
| 5,231,533 | A * | 7/1993 | Gonokami et al. ............ 359/328 |
| 5,244,636 | A | 9/1993 | Walt et al. |
| 5,244,813 | A | 9/1993 | Walt et al. |
| RE34,405 | E | 10/1993 | Gould et al. |
| 5,250,264 | A | 10/1993 | Walt et al. |
| 5,252,294 | A | 10/1993 | Kroy et al. |
| 5,252,494 | A | 10/1993 | Walt |
| 5,254,477 | A | 10/1993 | Walt |
| 5,281,370 | A | 1/1994 | Asher et al. |
| 5,298,741 | A | 3/1994 | Walt et al. |
| 5,302,509 | A | 4/1994 | Cheeseman |
| 5,306,618 | A | 4/1994 | Prober et al. |
| 5,308,771 | A | 5/1994 | Zhou et al. |
| 5,320,814 | A | 6/1994 | Walt et al. |
| 5,357,590 | A | 10/1994 | Auracher |
| 5,362,653 | A | 11/1994 | Carr et al. |
| 5,380,489 | A | 1/1995 | Sutton et al. |
| 5,405,784 | A | 4/1995 | Van Hoegaerden |
| 5,415,835 | A | 5/1995 | Brueck et al. |
| 5,422,246 | A | 6/1995 | Koopal et al. |
| 5,435,724 | A | 7/1995 | Goodman et al. |
| 5,444,330 | A | 8/1995 | Leventis et al. |
| 5,474,895 | A | 12/1995 | Ishii et al. |
| 5,480,723 | A | 1/1996 | Klainer et al. |
| 5,481,629 | A | 1/1996 | Tabuchi |
| 5,494,798 | A | 2/1996 | Gerdt et al. |
| 5,494,810 | A | 2/1996 | Barany et al. |
| 5,496,997 | A | 3/1996 | Pope |
| 5,498,392 | A | 3/1996 | Wilding et al. |
| 5,510,270 | A | 4/1996 | Fodor et al. |
| 5,512,490 | A | 4/1996 | Walt et al. |
| 5,516,635 | A | 5/1996 | Ekins et al. |
| 5,518,883 | A | 5/1996 | Soini |
| 5,532,128 | A | 7/1996 | Eggers et al. |
| 5,534,424 | A | 7/1996 | Uhlen et al. |
| 5,536,648 | A | 7/1996 | Kemp et al. |
| 5,545,531 | A | 8/1996 | Rava et al. |
| 5,552,270 | A | 9/1996 | Khrapko et al. |
| 5,556,752 | A | 9/1996 | Lockhart et al. |
| 5,565,324 | A | 10/1996 | Still et al. |
| 5,567,627 | A | 10/1996 | Lehnen |
| 5,573,909 | A | 11/1996 | Singer et al. |
| 5,575,849 | A | 11/1996 | Honda et al. |
| 5,585,069 | A | 12/1996 | Zanzucchi et al. |
| 5,587,128 | A | 12/1996 | Wilding et al. |
| 5,593,838 | A | 1/1997 | Zanzucchi et al. |
| 5,604,097 | A | 2/1997 | Brenner |
| 5,633,724 | A | 5/1997 | King et al. |
| 5,633,972 | A | 5/1997 | Walt et al. |
| 5,639,603 | A | 6/1997 | Dower et al. |
| 5,641,639 | A | 6/1997 | Perry |
| 5,650,489 | A | 7/1997 | Lam et al. |
| 5,652,059 | A | 7/1997 | Margel |
| 5,653,939 | A | 8/1997 | Hollis et al. |
| 5,656,241 | A | 8/1997 | Seufert et al. |
| 5,660,988 | A | 8/1997 | Duck et al. |
| 5,667,976 | A * | 9/1997 | Van Ness et al. ............ 435/6.12 |
| 5,674,698 | A | 10/1997 | Zarling et al. |
| 5,677,187 | A | 10/1997 | Anderson et al. |
| 5,679,524 | A | 10/1997 | Nikiforov et al. |
| 5,690,894 | A | 11/1997 | Pinkel et al. |
| 5,700,636 | A * | 12/1997 | Sheiness et al. ............ 435/6.11 |
| 5,700,897 | A | 12/1997 | Klainer et al. |
| 5,709,994 | A * | 1/1998 | Pease et al. ............ 435/4 |
| 5,723,218 | A | 3/1998 | Haugland et al. |
| 5,723,346 | A | 3/1998 | Frengen |
| 5,726,064 | A | 3/1998 | Robinson et al. |
| 5,744,305 | A | 4/1998 | Fodor et al. |
| 5,747,349 | A | 5/1998 | van den Engh et al. |
| 5,766,963 | A | 6/1998 | Baldwin et al. |
| 5,770,358 | A | 6/1998 | Dower |
| 5,779,976 | A | 7/1998 | Leland et al. |
| 5,783,401 | A | 7/1998 | Toledano |
| 5,800,992 | A | 9/1998 | Fodor |
| 5,807,755 | A | 9/1998 | Ekins |
| 5,814,524 | A | 9/1998 | Walt et al. |
| 5,830,663 | A | 11/1998 | Embleton et al. |
| 5,830,711 | A | 11/1998 | Barany et al. |
| 5,834,590 | A | 11/1998 | Vinik et al. |
| 5,837,551 | A | 11/1998 | Ekins |
| 5,840,256 | A | 11/1998 | Demers et al. |
| 5,846,595 | A * | 12/1998 | Sun et al. ............ 427/2.14 |
| 5,854,684 | A | 12/1998 | Stabile et al. |
| 5,855,753 | A | 1/1999 | Trau et al. |
| 5,856,083 | A | 1/1999 | Cheisky et al. |
| 5,858,534 | A * | 1/1999 | Sucholeiki ............ 428/407 |
| 5,858,732 | A | 1/1999 | Solomon et al. |
| 5,863,708 | A | 1/1999 | Zanzucchi et al. |
| 5,863,722 | A | 1/1999 | Brenner |
| 5,874,219 | A | 2/1999 | Rava et al. |
| 5,888,723 | A | 3/1999 | Sutton et al. |
| 5,900,481 | A | 5/1999 | Lough et al. |
| 5,922,617 | A * | 7/1999 | Wang et al. ............ 436/518 |
| 5,928,819 | A | 7/1999 | Crawford et al. |
| 5,939,021 | A | 8/1999 | Hansen et al. |
| 5,961,923 | A | 10/1999 | Nova et al. |
| 5,965,452 | A | 10/1999 | Kovacs |
| 5,989,835 | A | 11/1999 | Dunlay et al. |
| 6,013,456 | A | 1/2000 | Akhavan-Tafti |
| 6,023,540 | A * | 2/2000 | Walt et al. ............ 385/12 |
| 6,027,889 | A | 2/2000 | Barany et al. |
| 6,030,581 | A | 2/2000 | Virtanen |

(56) References Cited

U.S. PATENT DOCUMENTS

| | | | |
|---|---|---|---|
| 6,033,547 A | 3/2000 | Trau et al. | |
| 6,048,690 A | 4/2000 | Heller et al. | |
| 6,051,380 A | 4/2000 | Sosnowski et al. | |
| 6,054,564 A | 4/2000 | Barany et al. | |
| 6,074,754 A | 6/2000 | Jacobsen et al. | |
| 6,083,763 A | 7/2000 | Balch | |
| 6,084,991 A | 7/2000 | Sampas | |
| 6,090,545 A | 7/2000 | Wohlstadter et al. | |
| 6,090,912 A | 7/2000 | Lebl et al. | |
| 6,110,678 A | 8/2000 | Weisburg et al. | |
| 6,133,436 A | 10/2000 | Koster et al. | |
| 6,172,218 B1 | 1/2001 | Brenner et al. | |
| 6,200,737 B1 | 3/2001 | Walt et al. | |
| 6,210,891 B1 | 4/2001 | Nyren et al. | |
| 6,210,910 B1 | 4/2001 | Walt | |
| 6,251,639 B1 | 6/2001 | Kurn | |
| 6,258,568 B1 | 7/2001 | Nyren | |
| 6,266,459 B1 | 7/2001 | Walt et al. | |
| 6,268,148 B1 | 7/2001 | Barany et al. | |
| 6,274,320 B1 | 8/2001 | Rothberg et al. | |
| 6,327,410 B1 * | 12/2001 | Walt et al. | 385/115 |
| 6,355,431 B1 * | 3/2002 | Chee | C12Q 1/6813 435/6.11 |
| 6,406,845 B1 | 6/2002 | Walt et al. | |
| 6,420,169 B1 | 7/2002 | Read et al. | |
| 6,429,027 B1 | 8/2002 | Chee et al. | |
| 6,482,593 B2 | 11/2002 | Walt et al. | |
| 6,489,103 B1 | 12/2002 | Griffiths et al. | |
| 6,544,732 B1 | 4/2003 | Chee et al. | |
| 6,579,722 B1 | 6/2003 | Collins et al. | |
| 6,828,100 B1 | 12/2004 | Ronaghi | |
| 6,859,570 B2 * | 2/2005 | Walt et al. | 385/12 |
| 7,115,884 B1 | 10/2006 | Walt | |
| 7,166,431 B2 * | 1/2007 | Chee et al. | 435/6.11 |
| 7,291,504 B2 | 11/2007 | Seul | |
| 7,323,305 B2 | 1/2008 | Leamon et al. | |
| 2002/0122612 A1 | 9/2002 | Walt et al. | |
| 2002/0123043 A1 * | 9/2002 | Hutchens et al. | 435/6 |
| 2002/0197456 A1 | 12/2002 | Pope | |
| 2003/0027126 A1 | 2/2003 | Walt et al. | |
| 2003/0108867 A1 | 6/2003 | Chee | |
| 2003/0157499 A1 | 8/2003 | Lundeberg et al. | |
| 2003/0162217 A1 | 8/2003 | Rothberg et al. | |
| 2005/0064460 A1 | 3/2005 | Holliger et al. | |
| 2009/0170728 A1 * | 7/2009 | Walt et al. | 506/30 |
| 2011/0212848 A1 * | 9/2011 | Duffy et al. | 506/9 |

FOREIGN PATENT DOCUMENTS

| | | |
|---|---|---|
| CA | 2305545 | 4/1999 |
| CA | 2335951 | 12/1999 |
| EP | 0 269 764 A1 | 6/1988 |
| EP | 0 392 546 A2 | 10/1990 |
| EP | 0 478 319 A1 | 4/1992 |
| EP | 0 547 787 A1 | 6/1993 |
| EP | 0 633 465 A1 | 1/1995 |
| EP | 0 723 146 A1 | 7/1995 |
| EP | 0723148 | 7/1996 |
| GB | 2058379 | 4/1981 |
| GB | 2 294 319 A | 4/1996 |
| JP | 2-131569 A | 5/1990 |
| JP | 5-317030 A | 12/1993 |
| WO | WO 89/11101 A1 | 11/1989 |
| WO | WO 91/06678 | 5/1991 |
| WO | WO91/19023 | 12/1991 |
| WO | WO 93/02360 | 2/1993 |
| WO | WO93/06121 | 4/1993 |
| WO | WO 93/21340 | 10/1993 |
| WO | WO 93/23564 | 11/1993 |
| WO | WO93/24517 | 12/1993 |
| WO | WO 93/25563 | 12/1993 |
| WO | WO95/12608 | 5/1995 |
| WO | WO 96/03212 | 2/1996 |
| WO | WO96/04547 | 2/1996 |
| WO | WO96/07917 | 3/1996 |
| WO | WO 96/12962 | 5/1996 |
| WO | WO 97/12680 | 4/1997 |
| WO | WO 97/14028 | 4/1997 |
| WO | WO 97/31256 A2 | 8/1997 |
| WO | WO 97/31256 A3 | 8/1997 |
| WO | WO97/40383 | 10/1997 |
| WO | WO 97/40385 A1 | 10/1997 |
| WO | WO98/06007 | 2/1998 |
| WO | WO 98/13523 A1 | 4/1998 |
| WO | WO 98/40726 A1 | 9/1998 |
| WO | WO 98/50782 A2 | 11/1998 |
| WO | WO 98/50782 A3 | 11/1998 |
| WO | WO 98/53093 A1 | 11/1998 |
| WO | WO 98/53300 | 11/1998 |
| WO | WO 98/53300 A2 | 11/1998 |
| WO | WO 98/53300 A3 | 11/1998 |
| WO | WO 98/18434 A1 | 4/1999 |
| WO | WO 99/18434 A1 | 4/1999 |
| WO | WO99/19515 | 4/1999 |
| WO | WO 99/60170 A1 | 11/1999 |
| WO | WO 99/67414 A1 | 12/1999 |
| WO | WO 99/67641 A2 | 12/1999 |
| WO | WO 99/67641 A3 | 12/1999 |
| WO | WO00/03004 | 1/2000 |
| WO | WO00/04372 | 1/2000 |
| WO | WO 00/04372 A1 | 1/2000 |
| WO | WO 00/13004 A2 | 3/2000 |
| WO | WO 00/13004 A3 | 3/2000 |
| WO | WO 00/16101 A2 | 3/2000 |
| WO | WO 00/16101 A3 | 3/2000 |
| WO | WO 00/39587 A1 | 7/2000 |
| WO | WO 00/47996 A1 | 8/2000 |
| WO | WO 00/48000 A1 | 8/2000 |
| WO | WO 00/58516 | 10/2000 |
| WO | WO 00/63437 A2 | 10/2000 |
| WO | WO 00/63437 A3 | 10/2000 |
| WO | WO 00/71243 | 11/2000 |
| WO | WO 00/71992 | 11/2000 |
| WO | WO 00/71995 A2 | 11/2000 |
| WO | WO 00/71995 A3 | 11/2000 |
| WO | WO 00/75373 A2 | 12/2000 |
| WO | WO 00/75373 A3 | 12/2000 |

OTHER PUBLICATIONS

Egner, et al., "Tagging in combinatorial chemistry: The use of coloured and fluorescent beads" *Chem. Commun.* (1997) pp. 735-736.

"Fluorescent Microspheres (Tech. No. #19)," Bangs Laboratories (1997).

Fulton, et al., "Advanced multiplexed analysis with the FlowMetrix system" *Clinical Chemistry* (1997) 43(9): 1749-1756.

Giesig, et al., "Formation of ordered two-dimensional gold colloid lattices by electrophoretic desposition" *J. Phys. Chem.* (1993) 97: 6334-6336.

Grazia, et al., "In-vivo biomedical monitoring by Fiber-Optic System" *J. Lightwave Tech.* (1995) 13: 1396-1406.

Haab, et al., "Single Molecule Fluorescence Burst Detection of DNA Fragments Separated by Capillary Electrophoresis" *Anal. Chem.* (1995) 67(18): 3253-3256.

Micheletto, et al., *Langmuir* (1995) 11: 3333-3338.

"Microsphere Selection Guide" Bangs Laboratories, Inc. (Fisher, IN) (1998).

Nagayama, et al., *Phase Transitions* (1993) 45: 185-203.

Peterson, et al., "Fiber optic pH probe for physiological use" *Anal. Chem.* (1980) 52: 864-869.

Richetti, et al., *J. Physique Lettr.* (1984) 45: L-1137 to L-1143.

Schana, et al., "Quantitative Montioring of Gene Expression Patterns with a Complementary DNA Microarray" *Science* (1995) 270: 467-470.

Scott, et al., "Properties of fluorophores on solid phase resins; implications for screening, encoding and reaction monitoring" *Bioorganic & Medicinal Chem. Letters* (1997) 7(12): 1567-1572.

Seul, et al., "Domain Shapes and Patterns: The Phenomenology of modulated Phases" *Science* (1995) 267: 476-483.

(56) References Cited

OTHER PUBLICATIONS

Seul, et al., "Scale transformation of magnetic bubble arrays: coupling of topological disorder and polydispersity" *Science* (1993) 262: 558-560.
Sze, et al., "MIS Diode and Charge-Coupled Device" *The Physics of Semiconductors*, Chapter 7, pp. 362-430 (2$^{nd}$ Edition) (Wiley Interscience 1981).
Trau, et al, "Fiedld-Induced Layering of Colloidal Crystals" *Science* (1996) 272: 706-709.
Yeh, et al., "Assembly of ordered colloidal aggregates by electricfield-induced fluid flow" *Nature* (1997) 386: 57-59.
Abel, A., et al., "Fiber-optic evanescent wave biosensor for the detection of oligonucleotides," *Anal. Chem.* 68(17): 2905-2912, Sep. 1996.
Ahmadian et al., "Analysis of the p53 Tumor Suppressor Gene by Pyrosequencing," *BioTechniques*, 28(1): 140-4, 146-7, Jan. 2000.
Anonymous, "Fluorescent Microspheres," Tech. Note 19, Bang Laboratories, (Fishers, In) Feb. 1997.
Anonymous, "Microsphere Selection Guide," Bang Laboratories, (Fisher, In) Sep. 1998.
Bangs, L.B., "Immunological Applications of Microspheres," The Latex Course, Bangs Laboratories (Carmel, IN) Apr. 1996.
Barnard et al., "A Fibre-Optic Chemical Sensor with Discrete Sensing Sites," Nature, 353:338-340 (Sep. 1991).
Barshop et al., "Luminescent Immobilized Enzyme Test Systems for Inorganic Pyrophosphate: Assays Using Firefly Luciferase and Nicotinamide-Mononucleotide Adenylyl Transferase or Adenosine-5'-Triphosphate Sulfurylase," *Anal. Biochem.*, 197(1): 266-272, 1991.
Chen et al., "A Microsphere-Based Assay for Multiplexed Single Nucleotide Polymorphism Analysis Using Single Base Chain Extension," *Genome Research*, 10(4):549-557 (2000).
Cook et al., "A Rapid, Enzymatic Assay for the Measurement of Inorganic Pyrophosphate in Animal Tissues,"*Anal. Biochem.*, 91: 557-565, 1978.
Czarnik, "Illuminating the SNP Genomic Code," Modern Drug Discovery, 1(2):49-55 (1998).
Drake et al., "A New, Convenient Method for the Rapid Analysis of Inorganic Pyrophosphate," *Anal. Biochem.*, 94: 117-120, 1979.
Drmanac, R. et al., "Prospects for a Miniaturized, Simplified and Frugal Human Genome Project," Scientia Yugoslavica, 16(1-2):97-107 (1990).
Drmanac, R. et al., "Sequencing by Hybridization (SBH) with Oligonucleotide Probes as an Integral Approach for the Analysis of Complex Genomes," International Journal of Genome Research, 1(1):59-79 (1992).
Drmanac, R. et al., "Sequencing by Hybridization," Automated DNA Sequencing and Analysis, ed. M. Adams, C. Fields and J. Venter. (1994).
Drmanac, R. et al., "Sequencing by Oligonucleotide Hybridization: A Promising Framework in Decoding of the Genome Program," The First International Conference on Electrophoresis, Supercomputing and the Human Genome, Proceedings on Apr. 10-13, 1990 Conference at Florida State University. Ed. C. Cantor and H. Lim.
Ferguson et al., "A Fiber-Optic DNA Biosensor Microarray for the Analysis of Gene Expression," Nature Biotechnology, 14:1681-1684 (1996).
Fuh et al., "Single Fibre Optic Fluorescence pH Probe," Analyst, 112:1159-1163 (1987).
Guillory et al., "Measurement of Simultaneous Synthesis of Inorganic Pyrophosphate and Adenosine Triphosphate," *Anal. Biochem.*, 39: 170-180, 1971.
Healey et al., "Development of a Penicillin Biosensor Using a Single Optical Imaging Fiber," SPIE Proc. 2388:568-573 (1995).
Healey, et al. "Fiberoptic DNA Sensor Array Capable of Detecting Point Mutations." Analytical Biochemistry (1997), 251: 270-279.
Healey et al., "Improved Fiber-Optic Chemical Sensor for Penicillin," Anal. Chem. 67(24):4471-4476 (1995).
Hirschfeld et al., "Laser-Fiber-Optic 'Optrode' for Real Time In Vivo Blood Carbon Dioxide Level Monitoring," Journal of Lightwave Technology, LT-5(7):1027-1033 (1987).
Iannone et al., "Multiplexed Single Nucleotide Polymorphism Genotyping by Oligonucleotide Ligation and Flow Cytometry," Cytometry, 39:131-140 (2000).
Johnson et al., "An Enzyme Method for Determination of Inorganic Pyrophosphate and Its Use as an Assay for RNA Polymerase," *Anal. Biochem.*, 26: 137-145, 1968.
Jones, "An Iterative and Regenerative Method for DNA Sequencing," *BioTechniques*, 22: 938-946, May 1997.
Justesen et al., "Spectrophotometric Pyrophosphate Assay of 2',5'-Oligoadenylate Synthetase," *Anal. Biochem.*, 207(1): 90-93, 1992.
Karamohamed et al., "Real-Time Detection and Quantification of Adenosine Triphosphate Sulfurylase Activity by a Bioluminometric Approach," *Anal. Biochem.*, 271: 81-85, 1999.
Lust et al., "A Rapid, Enzymatic Assay for Measurement of Inorganic Pyrophosphate in Biological Samples," *Clin. Chimica Acta*, 66(2): 241-249, 1976.
Lyamichev et al., "Polymorphism identification and quantitative detection of genomic DNA by invasive cleavage of oligonucleotide probes," Nature Biotechnology, 17:292-296 (1999).
Metzker et al., "Termination of DNA synthesis by novel 3'-modified deoxyribonucleoside 5'-triphosphates," *Nucl. Acids Res.*, 22(20): 4259-4267, 1994.
Michael et al., "Fabrication of Micro- and Nanostructures Using Optical Imaging Fibers and Their Use as Chemical Sensors," Proc. 3$^{rd}$ Intl. Symp., Microstructures and Microfabricated Systems, ed. P.J. Hesketh, et al., v. 97-5, Electrochem. Sock., 152-157 (Aug. 1997).
Michael et al., "Making Sensors out of Disarray: Optical Sensor Microarrays," Proc. SPIE, 3270:34-41 (1998).
Michael et al., "Randomly Ordered Addressable High-Density Optical Sensor Arrays," Anal. Chem. 70(7):1242-1248 (Apr. 1998).
Mignani et al., "In-Vivo Biomedical Monitoring by Fiber-Optic Systems," Journal of Lightwave Technology, 13(7):1396-1406 (1995).
Nyren et al., "Detection of Single-Base Changes Using a Bioluminometric Primer Extension Assay," *Anal. Biochem.*, 244(2): 367-373, Jan. 1997.
Nyren, "Apyrase Immobilized on Paramagnetic Beads Used to Improve Detection Limits in Bioluminometric ATP Monitoring," *J Biolumin Chemilumin*, 9(1): 29-34, Jan.-Feb. 1994.
Nyren et al., "Solid Phase DNA Minisequencing by an Enzymatic Luminometric Inorganic Pyrophosphate Detection Assay," *Anal. Biochem.*, 208(1): 171-175, Jan. 1993.
Nyren et al., "Enzymatic Method for Continuous Monitoring of Inorganic Pyrophosphate Synthesis," *Anal. Biochem.*, 151: 504-509, 1985.
Pantano et al., "Ordered Nanowell Arrays," Chem. Mater., 8(12):2832-2835 (1996).
Peterson et al., "Fiber-Optic Sensors for Biomedical Applications," Science, 12:123-127 (1984).
Peterson, J. et al., "Fiber Optic pH Probe for Physiological Use," Anal. Chem., 52:864-869 (1980).
Piunno et al., "Fiber-Optic DNA Sensor for Fluorometric Nucleic Acid Determination," Anal. Chem., 67:2635-2643 (1995).
Pope, E. "Fiber Optic Chemical Microsensors Employing Optically Active Silica Microspheres," SPIE, 2388:245-256 (1995).
Reeves et al., "Enzymatic Assay Method for Inorganic Pyrophosphate," *Anal. Biochem.*, 28: 282-287, 1969.
Ronaghi et al., "Analyses of Secondary Structures in DNA by Pyrosequencing," *Anal. Biochem.*, 267(1): 65-71, Feb. 1999.
Ronaghi et al., "A Sequencing Method Based on Real-Time Pyrophosphate," *Science*, 281(5375): 363, 365, Jul. 1998.
Ronaghi et al., "Real-Time DNA Sequencing Using Detection of Pyrophosphate Release," *Anal. Biochem.*, 242(1) 84-89, Nov. 1996.
Shoemaker, et al. "Quantitative Phenotypic Analysis of Yeast Deletion Mutants Using a Highly Parallel Molecular Bar-Coding Strategy." Nature Genetics (1996), 14: 450-456.
Strachan et al., "A Rapid General Method for the Identification of PCR Products Using a Fibre-Optic Biosensor and its Application to the Detection of Listeria," Letters in Applied Microbiology, 21:5-9 (1995).

(56) References Cited

OTHER PUBLICATIONS

Walt, D., "Fiber-Optic Sensors for Continuous Clinical Monitoring," Proc. IEEE, 80(6):903-911 (1992).

Walt, et al. "Fiber Optic Imaging Sensors." Accounts of Chemical Research (1998), 31: 267-278.

Walt et al., "Self-Regenerating Fiber-Optic Sensors" Liquid Crystalline Polymer Systems, American Chemical Society, Jan. 1, 1995, vol. 586, pp. 186-196.

* cited by examiner

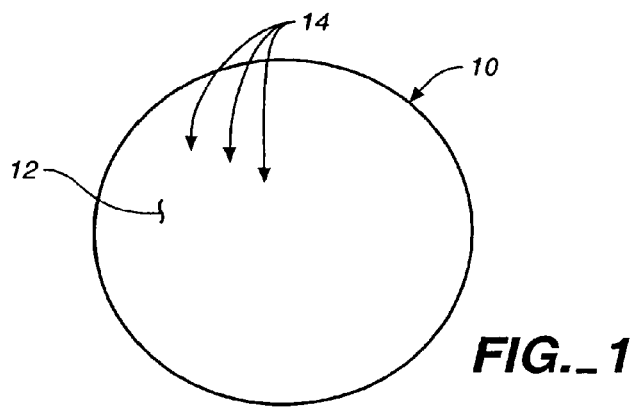
FIG._1
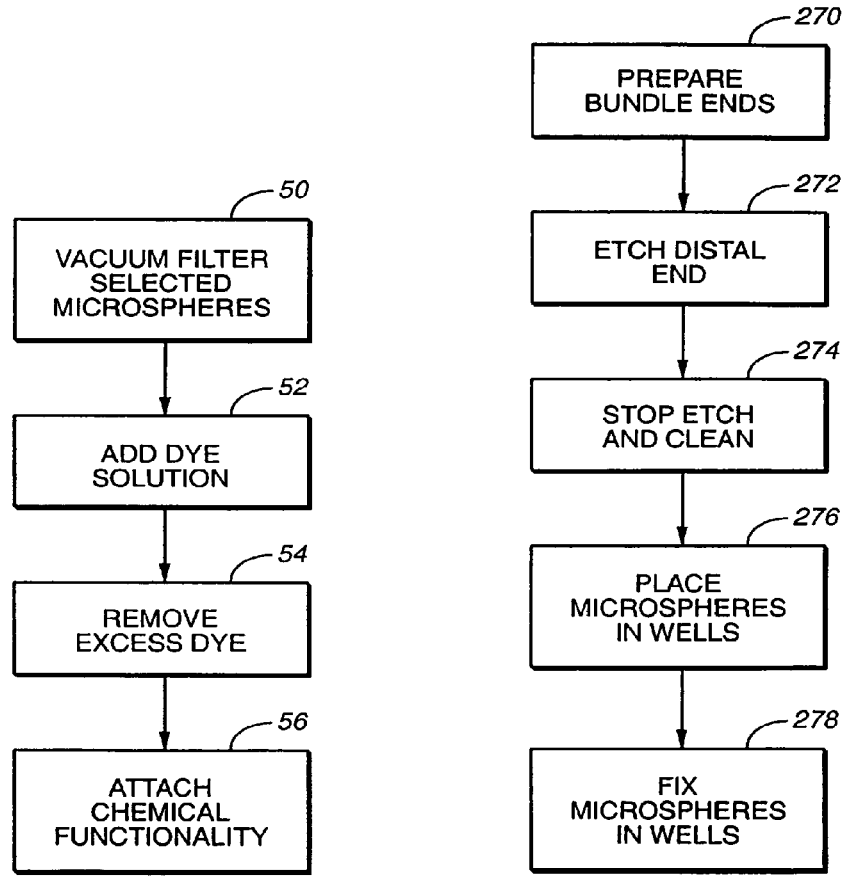
FIG._2    FIG._6

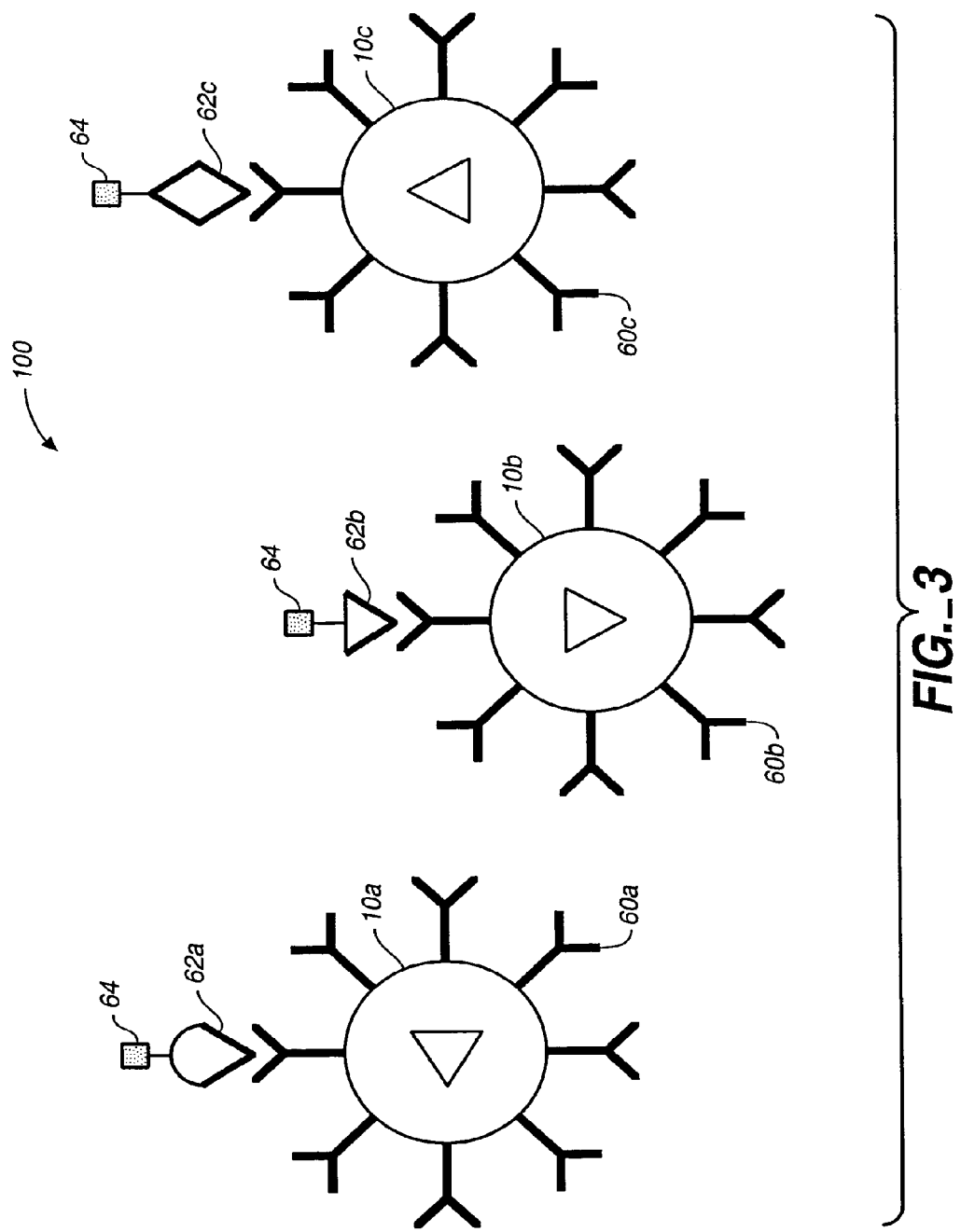
FIG._3

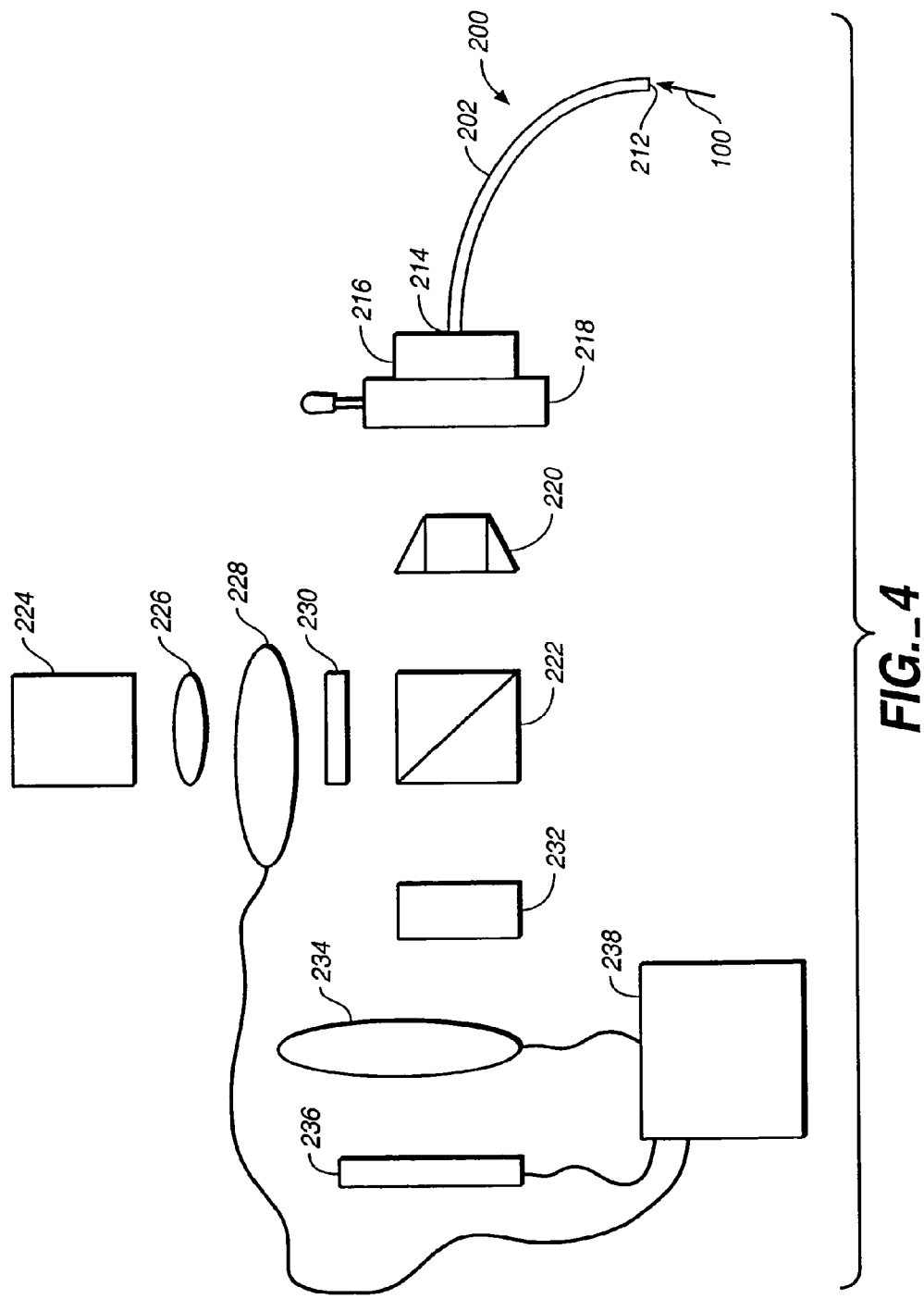
FIG._4

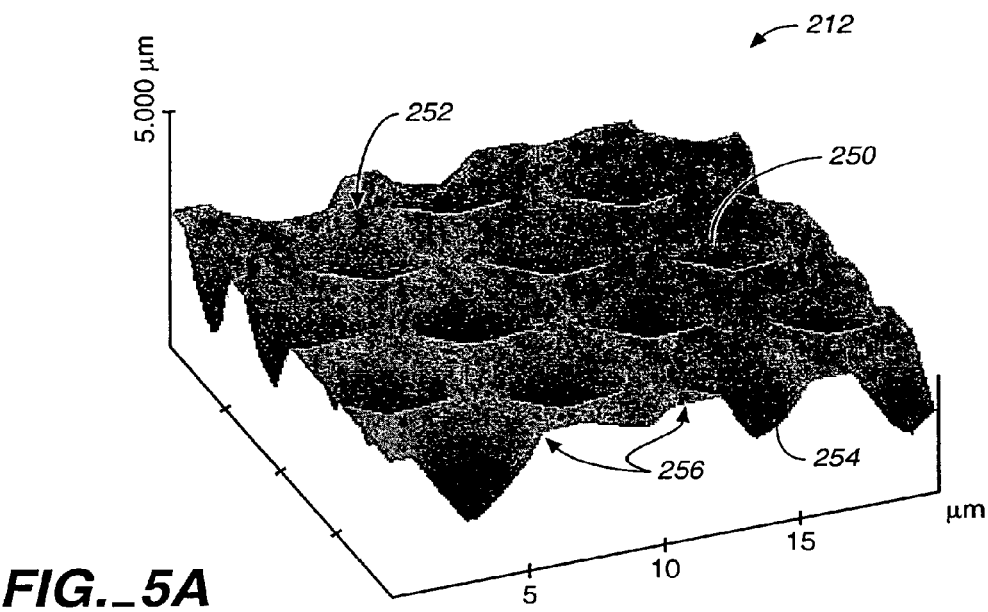
FIG._5A
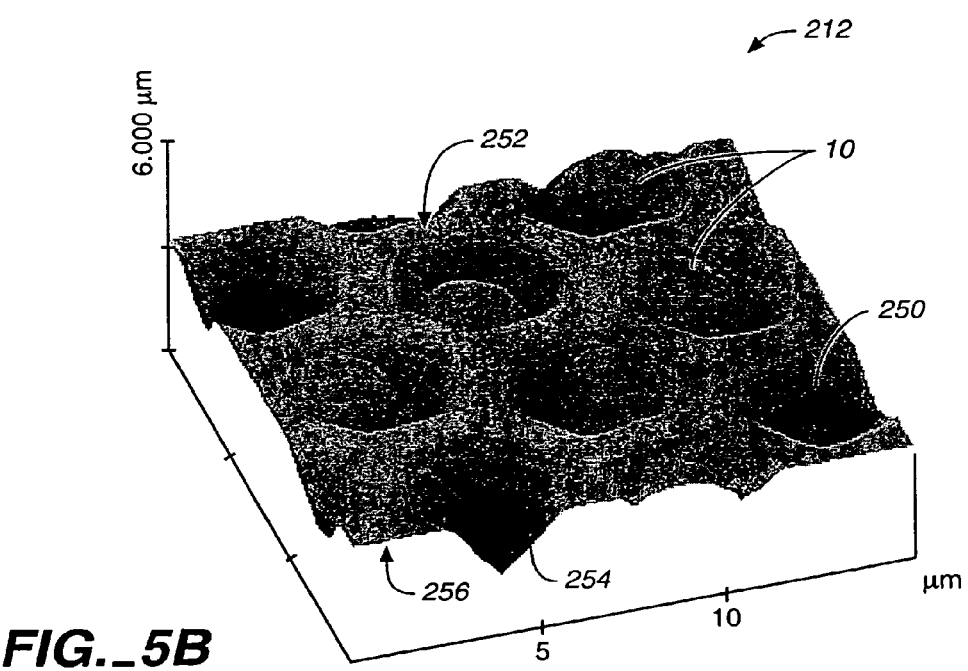
FIG._5B

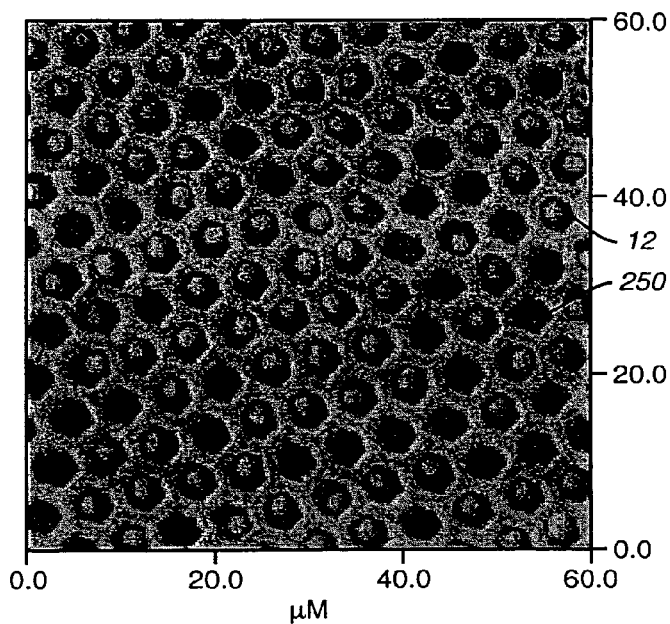
FIG._7A
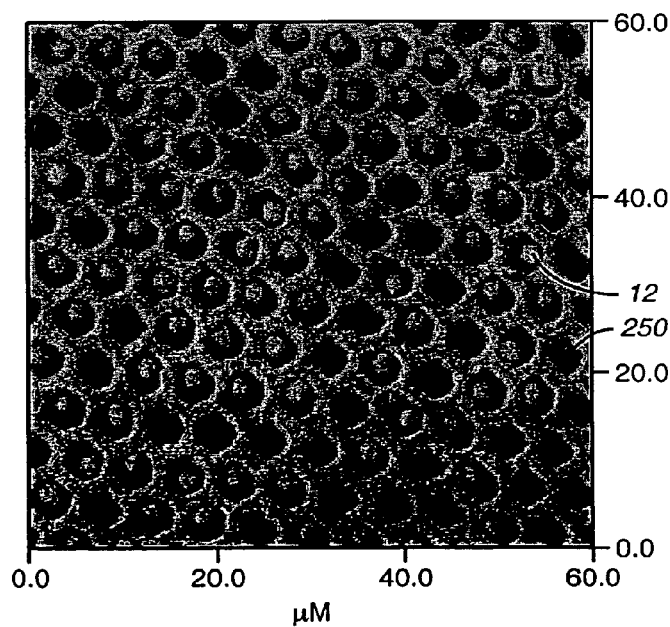
FIG._7B

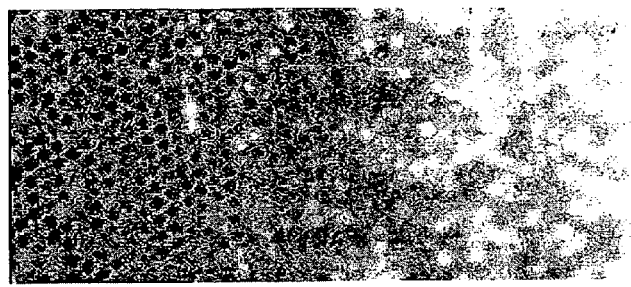
FIG._8A
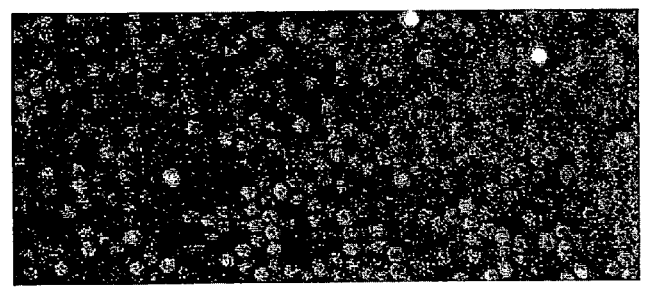
FIG._8B
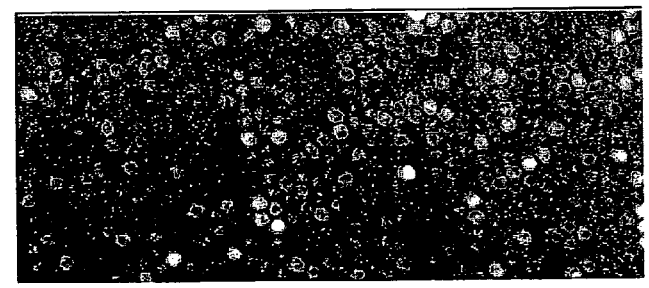
FIG._8C

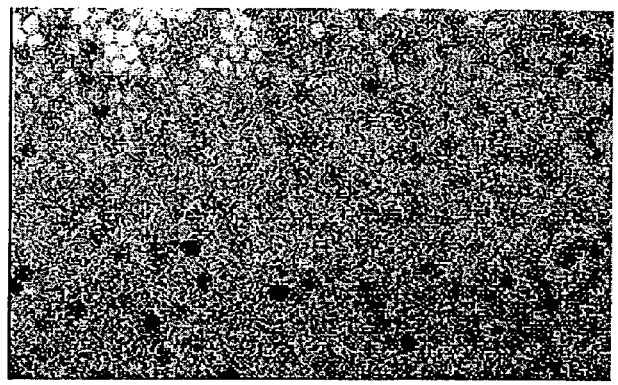
*FIG._9A*
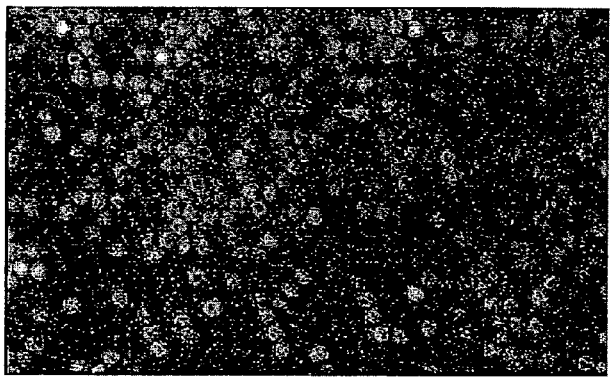
*FIG._9B*
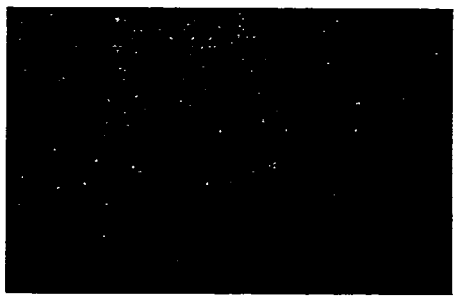 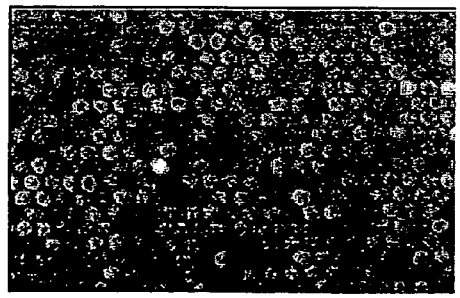
*FIG._10A*　　　　　　*FIG._10B*

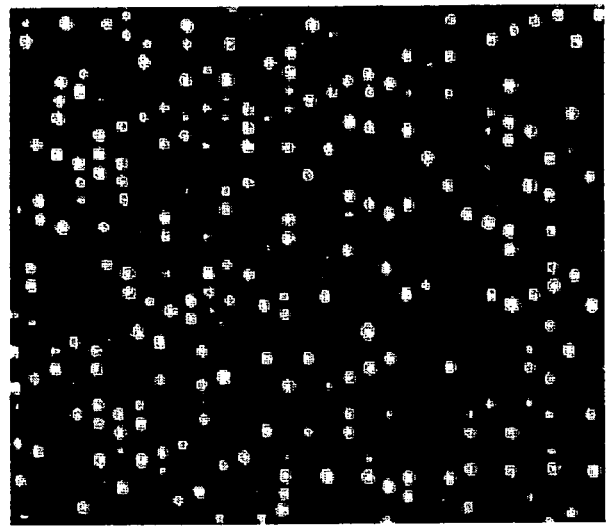
FIG._11A
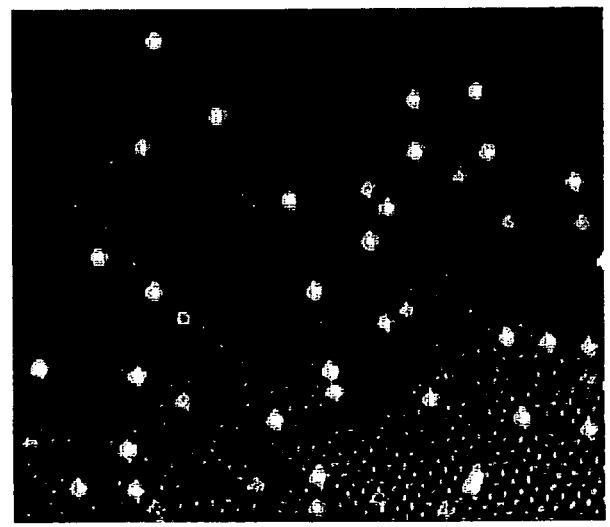
FIG._11B

Mean: 143.8
S.D.: 39.4
C.V.: 27.3%
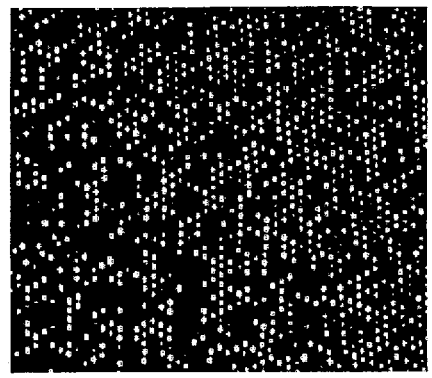
FIG._12A
Mean: 167.3
S.D.: 45.7
C.V.: 27.3%
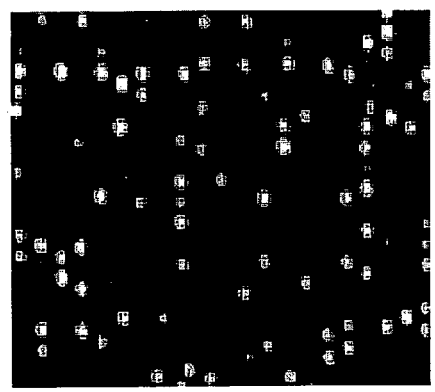
FIG._12B
Mean: 198.9
S.D.: 38.3
C.V.: 19.3%
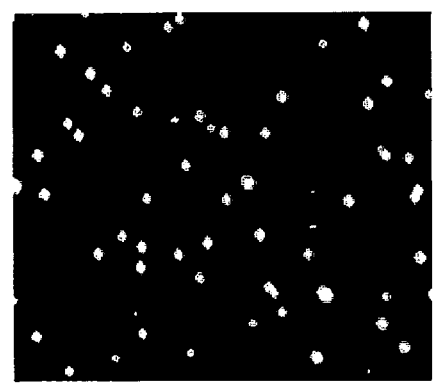
FIG._12C

METHODS FOR DETECTING TARGET ANALYTES AND ENZYMATIC REACTIONS

CROSS-REFERENCE TO RELATED APPLICATIONS

This application is a continuation of U.S. Ser. No. 12/265,697, filed Nov. 5, 2008, which is a continuation of U.S. Ser. No. 10/920,637, filed Aug. 17, 2004, now U.S. Pat. No. 7,622,294, issued Nov. 24, 2009. U.S. Ser. No. 10/920,637 is a continuation-in-part of U.S. Ser. No. 09/786,896, filed Sep. 10, 1999, now abandoned, which is a national phase application of PCT application U.S. 99/20914, which claims priority of U.S. Ser. No. 09/151,877, filed Sep. 11, 1998, now U.S. Pat. No. 6,327,410, issued Dec. 4, 2001, which is a continuation-in-part of U.S. Ser. No. 08/818,199, filed Mar. 14, 1997, now U.S. Pat. No. 6,023,540, issued Feb. 8, 2000. U.S. Ser. No. 10/920,637 is also a continuation-in-part of U.S. Ser. No. 09/840,012, filed Apr. 20, 2001, now abandoned, which is a continuation of U.S. Ser. No. 09/450,829, filed Nov. 29, 1999, now U.S. Pat. No. 6,266,459, issued Jul. 24, 2001, which is a continuation of U.S. Ser. No. 08/818,199, filed Mar. 14, 1997, now U.S. Pat. No. 6,023,540, issued Feb. 8, 2000. U.S. Ser. No. 10/920,637 is also a continuation-in-part of U.S. Ser. No. 09/925,292, filed Aug. 8, 2001, now U.S. Pat. No. 6,859,570, issued Feb. 22, 2005, which is a continuation of U.S. Ser. No. 09/151,877, filed Sep. 11, 1998, now U.S. Pat. No. 6,327,410, issued Dec. 4, 2001, which is a continuation-in-part of U.S. Ser. No. 08/818,199, filed Mar. 14, 1997, now U.S. Pat. No. 6,023,540, issued Feb. 8, 2000. U.S. Ser. No. 10/920,637 is also a continuation-in-part of U.S. Ser. No. 09/816,651, filed Mar. 23, 2001, now abandoned, which is a continuation of U.S. Ser. No. 09/450,829, filed Nov. 29, 1999, now U.S. Pat. No. 6,266,459, issued Jul. 24, 2001, which is a continuation of U.S. Ser. No. 08/818,199, filed Mar. 14, 1997, now U.S. Pat. No. 6,023,540, issued Feb. 8, 2000. All of the above patent applications are expressly incorporated herein by reference.

BACKGROUND OF THE INVENTION

The use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electra-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wollbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the Properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength $\lambda_{ab}$; reach an excited energy state; and subsequently emit light at another light wavelength, $\lambda_{em}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W.H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analyses of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acta.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talante* 35:109 (1988); Munkholm et al., *Anal. Chem.* 58:1427 (1986); Seitz, W. R., *Anal. Chem.* 56:16A-34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun at al., *Anal. Chem. Acta.* 160:47 (1984); Schwab, et al., *Anal. Chem.* 56:2199 (1984); Wolfbeis, O. S., "Fiber Optic Chemical Sensors", Ed. CRC Press, Boca Raton, Fla., 1991, 2nd Volume; and Pantano, P., Walt, D. R., *Anal. Chem.,* 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

In the two previous patents multiple chemical functionalities were placed at the end of a single optical fiber bundle sensor. This configuration yielded an analytic chemistry sensor that could be remotely monitored via the typically small bundle. A potential drawback, however, was the difficulty in applying the various chemistries associated with the chemical functionalities; the functionalities were built on the sensor in a serial fashion. Accordingly, compositions and methods are desirable that allow the generation of large arrays that can be either encoded or decoded to allow the detection of target analytes. The arrays can be fiber optic arrays or arrays on other array substrates and can include microspheres.

SUMMARY OF THE INVENTION

Accordingly, in one aspect the invention provides a method of detecting a target analyte in a sample comprising providing an array comprising an array substrate, wherein the array substrate is other than a fiber optic bundle, and at least first and second sites wherein first and second reaction components are immobilized at said first and second sites, respectively, contacting said array substrate with the sample and detecting a change in an optical property around at least the first site as an indication of the interaction between the target analyte and at least the first reaction component.

In addition the invention provides a method of detecting a target analyte in a sample comprising providing an array comprising an array substrate comprising discrete sites and a population of microspheres comprising at least first and second reaction components respectively and a detection molecule. The method further includes contacting the array with the sample and detecting a change in an optical property around at least the first microsphere as an indication of the interaction between the target analyte and at least the first reaction component.

The invention also provides a method of detecting an enzymatic reaction comprising providing an array comprising an array substrate comprising discrete sites, and a population of microspheres randomly distributed on the array substrate, wherein the microspheres comprise at least one enzyme, contacting the array with a sample comprising a target analyte, wherein the target analyte is an enzyme substrate, monitoring a signal in a region surrounding the microspheres, whereby detection of the signal provides an indication of the reaction between the enzyme and the enzyme substrate.

In addition the invention provides a method of detecting an enzymatic reaction comprising providing an array comprising an array substrate comprising discrete sites and a population of microspheres randomly distributed on said array substrate, the population comprising first and second subpopulations, wherein the first and second subpopulations comprise first and second discrete oligonucleotides, respectively, attached to the microspheres, contacting the array with a composition comprising an enzyme, monitoring a signal in a region surrounding the microspheres, whereby detection of the signal provides an indication of the reaction between the enzyme and at least one of the discrete oligonucleotides.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a schematic diagram illustrating the optical signature encoding and chemical functionalizing of the microspheres according to the present invention;

FIG. 2 is a process diagram describing the preparation, encoding, and functionalizing of the microspheres of the present invention;

FIG. 3 is a schematic diagram illustrating a microsphere system including microspheres with different chemical functionalities and encoded descriptions of the functionalities;

FIG. 4 is a schematic diagram of the inventive fiber optic sensor and associated instrumentation and control system;

FIGS. 5A and 5B are micrographs illustrating the preferred technique for attaching or affixing the microspheres to the distal end of the optical fiber bundle;

FIG. 6 is a process diagram describing well formation in the optical fiber bundle and affixation of the microspheres in the wells;

FIGS. 7A and 7B are micrographs showing the array of microspheres in their corresponding wells prior and subsequent to physical agitation, tapping and air pulsing, demonstrating the electrostatic binding of the microspheres in the wells;

FIGS. 8A, 8B, and 8C are micrographs from alkaline phosphatase microspheres when exposed to fluorescein diphosphate, at the fluorescein emission wavelength, at an encoding wavelength for DOC, and at an encoding wavelength for TRC, respectively;

FIGS. 9A and 9B are micrographs showing the optical signal from β-galactosidase microspheres when exposed to fluorescein β-galactopyranoside at the fluorescein emission wavelength and at an encoding wavelength for DiIC, respectively; and FIGS. 10A and 10B are micrographs showing the optical response from rabbit antibody microspheres prior to and post, respectively, exposure to fluorescein labeled antigens.

FIGS. 11A and 11B are micrographs depicting the optical response from beads synthesized with DNA on the bead surface, following a 10 min. hybridization with a Cy3-labeled probe complementary to the sequence of the DNA immobilized on the bead. Beads were randomly distributed on A) an etched optical imaging fiber or B) a patterned polymer (polyurethane) substrate (a chip). Following hybridization with 5 nM Cy3-labeled probe, the substrates were placed in buffer for optical readout on an imaging system. A) was imaged through the proximal end, with the distal (beaded) end in buffer solution. B) was imaged directly from the top, through a coverslip.

FIGS. 12A, 12B and 12C are micrographs depicting the optical responses between different substrates. The substrate in A) and B) is an etched optical imaging fiber, and the substrate in C) is a chip. Data were obtained as described in FIG. 11, and quantified to determine mean intensity and variability.

DETAILED DESCRIPTION OF THE PREFERRED EMBODIMENTS

The present invention is based on the combination of high-density arrays and a novel detection mechanism wherein labels or signals are detected on an array in a region surrounding a site on the array. That is, previously, detection on arrays involved the detection of targets while the targets were attached to the array or array substrate. However, the present invention provides methods and compositions for monitoring the presence of a target analyte by detecting a change in an optical property around at least a first discrete site on an array.

In one embodiment, the present invention is based on two synergistic inventions: 1) the development of a bead-based analytic chemistry system in which beads, also termed microspheres, carrying different chemical functionalities may be mixed together while the ability is retained to identify the functionality of each bead using an optically interrogatable encoding scheme (an "optical signature"); and 2) the use of a substrate comprising a patterned surface containing individual sites that can bind or associate individual beads. In preferred embodiments the substrate is patterned. This allows the synthesis of the bioactive agents (i.e. compounds such as nucleic acids and antibodies) to be separated from their placement on an array, i.e. the bioactive agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

Accordingly, the present invention provides array compositions comprising at least a first substrate with a surface comprising individual sites. By "array" herein is meant a plurality of bioactive agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 50,000 being particularly preferred, and from about 20,000 to about 30,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 nm can be used, and very small fibers are known, it is possible to have as many as 250,000 different fibers and beads in a 1 mm$^2$ fiber optic bundle, with densities of greater than 15,000,000 individual beads and fibers per 0.5 cm$^2$ obtainable.

The compositions comprise a substrate. By "substrate", "array substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, composite materials, ceramics, and plastic resins, silica or silica-based materials including silicon and modified silicon, carbon, metals, inorganic glasses, plastics, optical fiber bundles, and a variety of other polymers. In general, the substrates allow optical detection and do not appreciably fluoresce.

In one embodiment, the substrate does not comprise the ends of an optical fiber bundle.

In one embodiment, the substrate is planar, although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In one embodiment, at least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In one embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In one embodiment, physical alterations are made in a surface of the substrate to produce the sites. In a preferred embodiment, the substrate is a fiber optic bundle and the surface of the substrate is a terminal end of the fiber bundle. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

In this embodiment, the microspheres suitably are non-covalently associated in the wells, although the wells may additionally be chemically functionalized as is generally described below, cross-linking agents may be used, or a physical barrier may be used, i.e. a film or membrane over the beads.

In a further embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either bioactive agent attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

FIG. 1 illustrates the construction of a bead or microsphere 10 according to the principles of the present invention. In common with the prior art, the microsphere 10 is given a bioactive agent 12, which is typically applied to the microsphere's surface. The bioactive agent is designed so that in the presence of the analyte(s) to which it is targeted, an optical signature of the microsphere, possibly including region surrounding it, is changed.

It should be noted that a key component of the invention is the use of a substrate/bead pairing that allows the association or attachment of the beads at discrete sites on the surface of the substrate, such that the beads do not move during the course of the assay.

In one embodiment each microsphere comprises two components: a bioactive agent and an optical signature.

By "candidate bioactive agent" or "bioactive agent" or "chemical functionality" or "binding ligand" herein is meant as used herein describes any molecule, e.g., protein, oligopeptide, small organic molecule, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic adds" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, *J. Org. Chem.*, 35:3800 (1970); Sprinzl, et al., *Eur. J. Biochem.*, 81:579 (1977); Letsinger, et al, *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, at al., *J. Am. Chem. Soc.*, 111:2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al, *Nature*, 380:207 (1996), all of which are incorporated by reference)). Other analog nucleic acids include those with positive backbones (Denpcy, of al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed.*

English, 30:423 (1991); Letsinger, et al. *J. Am. Chem. Soc.*, 110:4470 (1988); Letsinger, et al., *Nucleosides & Nucleotides*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic adds (see Jenkins, of al., *Chem. Soc. Rev.*, (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and basepair analogs such as nitropyrrole and nitroindole, etc.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point $(T_m)$ for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres are listed in Table I.

TABLE I

| Surface chemistry | Name: |
|---|---|
| NH$_2$ | Amine |
| COOH | Carboxylic Acid |
| CHO | Aldehyde |
| CH$_2$—NH$_2$ | Aliphalic Amine |
| CO NH$_2$ | Amide |
| CH$_2$—Cl | Chloromethyl |
| CONH—NH$_2$ | Hydrazide |
| OH | Hydroxyl |
| SO$_4$ | Sulfate |
| SO$_3$ | Sulfonate |
| Ar NH$_2$ | Aromatic Amine |

These functional groups can be used to add any number of different bioactive agents to the beads, generally using known chemistries. For example, bioactive agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the bioactive agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the bioactive agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems.* 7(4):275-308 (1991), expressly incorporated herein). Proteinaceous bioactive agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the bioactive agents may be attached in a variety of ways, including those listed above. What is important is that manner of attachment does not significantly alter the functionality of the bioactive agent; that is, the bioactive agent should be attached in such a flexible manner as to allow its interaction with a target.

Specific techniques for immobilizing enzymes on microspheres are known in the prior art. In one case, NH$_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant) −0.02%, and rinsed again with a pH 7.7 PBS plus 0.01% tween 20. Finally, the enzyme is added to the solution, preferably after being prefiltered using a 0.45 µm amicon micropure filter.

In addition to a bioactive agent, the microspheres comprise an optical signature that can be used to identify the attached bioactive agent. That is, each subpopulation of microspheres comprise a unique optical signature or optical tag that can be used to identify the unique bioactive agent of that subpopulation of microspheres; a bead comprising the unique optical signature may be distinguished from beads at other locations with different optical signatures. As is outlined herein, each bioactive agent will have an associated unique optical signature such that any microspheres comprising that bioactive agent will be identifiable on the basis of the signature. As is more fully outlined below, it is possible to reuse or duplicate optical signatures within an array, for example, when another level of identification is used, for example when beads of different sizes are used, or when the array is loaded sequentially with different batches of beads.

In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique tags may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 1989-1991 Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another, thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the bead matrix or pores of the beads. Referring to the embodiment of FIG. 1, reporter dyes 14 are added to the microsphere 10 with the encoding occurring in the ratio of two or more dyes. The reporter dyes 14 may be chromophore-type. Fluorescent dyes, however, are preferred because the strength of the fluorescent signal provides a better signal-to-noise ratio when decoding. Additionally, encoding in the ratios of the two or more dyes, rather than single dye concentrations, is preferred since it provides insensitivity to the intensity of light used to interrogate the reporter dye's signature and detector sensitivity.

In one embodiment, the dyes are added to the bioactive agent, rather than the beads, although this is generally not preferred.

FIG. 2 is a process diagram illustrating the preparation of the microspheres. In step 50, an aliquot of stock microspheres are vacuum filtered to produce a dry cake. In one implementation, microsphere copolymers of methylstyrene (87%) and divinylbenzene (13%) are used that have a 3.1 micrometer (μm) diameter. The dry cake is then broken apart and a dye solution added to it in step 52 to encode optical signatures of the microspheres with information concerning the intended surface chemical functionalities. Dyes may be covalently bonded to the microspheres' surface, but this consumes surface binding sites desirably reserved for the chemical functionalities. Preferably, the microspheres are placed in a dye solution comprising a ratio of two or more fluorescent reporter dyes dissolved in an organic solvent that will swell the microspheres, e.g., dimethylformamide (DMF). The length of time the microspheres are soaked in the dye solution will determine their intensity and the broadness of the ratio range.

In an exemplary two dye system, Texas Red Cadaverine (TRC) is used, which is excited at $\lambda_{ab}$=580 mm and emits at $\lambda_{em}$=630 mm, in combination with indodicarbocyanine (Di1C): 610/670 ($\lambda_{ab}/\lambda_{em}$). Generally, dyes are selected to be compatible with the chemistries involved in the analysis and to be spectrally compatible. This avoids deconvolution problems associated with determining signal contributions based on the presence of both the analyte and the encoding dye ratios contributing to an overlapping emission spectral region.

Examples of other dyes that can be used are Oxazin (662/705), IR-144 (745/825), IR-140 (776/882), IR-125 (786/800) from Exciton, and Bodipy 665/676 from Molecular Probes, and Naphthofluorescein (605/675) also from Molecular Probes. Lathanide complexes may also be used. Fluorescent dyes emitting in other than the near infrared may also be used. Chromophore dyes are still another alternative that produce an optically interrogatable signature, as are more exotic formulations using Raman scattering-based dyes or polarizing dyes, for example. The ability of a particular dye pair to encode for different chemical functionalities depends on the resolution of the ratiometric measurement. Conservatively, any dye pair should provide the ability to discriminate at least twenty different ratios. The number of unique combinations of two dyes made with a particular dye set is shown in the following Table II.

TABLE II

| Number of dyes in set | Combinations possible |
| --- | --- |
| 3 | 3 |
| 4 | 6 |
| 5 | 10 |
| 6 | 15 |

Thus, using six dyes and twenty distinct ratios for each dye pair, 300 separate chemical functionalities may be encoded in a given population of microspheres. Combining more than two dyes provides additional diversity in the encoding combinations. Furthermore, the concentration of the dyes will contribute to their intensity; thus intensity is another way to increase the number of unique optical signatures.

In step 54, the microspheres are vacuum filtered to remove excess dye. The microspheres are then washed in water or other liquid that does not swell the microspheres, but in which the dyes are still soluble. This allows the residual dye to be rinsed off without rinsing the dye out of the microspheres.

In step 56, the bioactive agent is attached to the microsphere surface if not already present. It should be understood that surface chemistries may be present throughout the microsphere's volume, and not limited to the physical circumferential surface.

Once the microspheres are made comprising at least one bioactive agent and an optical signature, the microspheres are added to discrete sites on the surface of the substrate. This can be done in a number of ways, but generally comprises adding the beads to the surface under conditions that will allow the association of the microspheres on or at the discrete sites. The association of the beads on the surface may comprise a covalent bonding of the bead to the surface, for example when chemical attachment sites are added to both the substrate and the bead; an electrostatic or hydroaffinity, when charge, hydrophobicity or hydrophilicity is used as the basis of the binding; a physical yet non-covalent attachment such as the use of an adhesive; or a spatial attachment, for example the localization of a bead within a well. In some embodiments it may be preferable to effect a more permanent attachment after the initial localization, for example through the use of cross-linking agents, a film or membrane over the array.

FIG. 3 schematically illustrates a microsphere system, or array of microspheres, 100 formed from microsphere populations that have different bioactive agents. While a large number of microspheres and bioactive agents may be employed, in this example only three microsphere populations are shown. The individual populations, or subpopulations, of microspheres are represented as 10a, 10b, 10c carrying respective bioactive agents or probe sequences 60a, 60b, 60c, as exemplary functionalities. The subpopulations may be combined in either a random or ordered fashion on a substrate, with a corresponding distribution of their respective bioactive agents.

Typically, with conventional methods, mixing microsphere populations having different bioactive agents results in the loss of information regarding the selectivity for each of the corresponding target sequences. In a solution of microspheres with each of the probe sequences 60a, 60b, and 60c, it is possible to determine that at least one of the target sequences 62a, 62b, and 62c is present when a fluorescent marker dye 64 concentration is observed on the microspheres 10. However, with conventional approaches, typically there is no way to determine which bioactive agent or probe sequence 60a, 60b, and 60c is generating the activity since the information concerning which microsphere contained which probe sequence was lost when the subpopulations were mixed.

However, with the microsphere system 100 and method of the present invention, each microsphere in each subpopulation is encoded with a common optical signature. In the illustrated example, the subpopulation represented by microsphere 10a has a two reporter dye ratio of 10:1; the subpopulation of microspheres 10b has a ratio of 1:1 of the same reporter dyes, and subpopulation of microspheres 10c has a ratio of 1:10 of the reporter dyes.

Thus, the randomly mixed subpopulations of microspheres are useful as an analytic chemistry system based on each of the carried bioactive agents 60a-60c separately. The microsphere array or system 100 is exposed to an analyte of interest to which some of the bioactive agents may interact. Any interaction changes the optical response of the corresponding microspheres by, for example, binding a fluorescent dye 64 to the microspheres. By identifying the chemical functionalities of the microsphere in which the optical signature has changed, using the encoded dye combinations, information regarding the chemical identity and concentration of an analyte may be gained based upon the interaction or noninteraction of each bioactive agent contained in the microsphere system 100.

The microspheres exhibiting activity or changes in their optical signature may be identified by a conventional optical train and optical detection system. Decoding can also be performed either manually or automatically with the aid of a computer. Depending on the particular encoding or reporter dyes used and their operative wavelengths, optical filters designed for a particular wavelengths may be employed for optical interrogation of the microspheres of bioactive agents. In a preferred embodiment, the analytic chemistry microsphere system is used in conjunction with an optical fiber bundle or fiber optic array as a substrate.

FIG. 4 is a schematic block diagram showing a microsphere-based analytic chemistry system employing a fiber optic assembly 200 with an optical detection system. The fiber optic assembly 200 comprises a fiber optic bundle or array 202, that is constructed from clad fibers so that light does not mix between fibers. A microsphere array or system, 100 is attached to the bundle's distal end 212, with the proximal end 214 being received by a z-translation stage 216 and x-y micropositioner 218. These two components act in concert to properly position the proximal end 214 of the bundle 202 for a microscope objective lens 220. Light collected by the objective lens 220 is passed to a reflected light fluorescence attachment with three pointer cube slider 222. The attachment 222 allows insertion of light from a 75 Watt Xe lamp 224 through the objective lens 220 to be coupled into the fiber bundle 202. The light from the source 224 is condensed by condensing lens 226, then filtered and/or shuttered by filter and shutter wheel 228, and subsequently passes through a ND filter slide 230.

Light returning from the distal end 212 of the bundle 202 is passed by the attachment 222 to a magnification changer 232 which enables adjustment of the image size of the fiber's proximal or distal end. Light passing through the magnification changer 232 is then shuttered and filtered by a second wheel 234. The light is then imaged on a charge coupled device (CCD) camera 236. A computer 238 executes imaging processing software to process the information from the CCD camera 236 and also possibly control the first and second shutter and filter wheels 228, 234. The instrumentation exclusive of the fiber sensor 200, i.e., to the left of the proximal end of the bundle 202 is discussed more completely by Bronk, et al., Anal. Chem. 1995, Vol. 67, number 17, pp. 2750-2752.

The microsphere array or system 100 may be attached to the distal end of the optical fiber bundle using a variety of compatible processes. It is important that the microspheres are located close to the end of the bundle. This ensures that the light returning in each optical fiber predominantly comes from only a single microsphere. This feature is necessary to enable the interrogation of the optical signature of individual microspheres to identify reactions involving the microsphere's functionality and also to decode the dye ratios contained in those microspheres. The adhesion or affixing technique, however, must not chemically insulate the microspheres from the analyte.

FIGS. 5A and 5B are micrographs of the distal end 212 of the bundle 202 illustrating the preferred technique for attaching the microspheres 10 to the bundle 202. Wells 250 are formed at the center of each optical fiber 252 of the bundle 202. As shown in FIG. 5B, the size of the wells 250 are coordinated with the size of the microspheres 10 so that the microspheres 10 can be placed within the wells 250. Thus, each optical fiber 252 of the bundle 202 conveys light from the single microsphere 10 contained in 5 its well. Consequently, by imaging the end of the bundle 202 onto the CCD array 236, the optical signatures of the microspheres 10 are individually interrogatable.

FIG. 6 illustrates how the microwells 250 are formed and microspheres 10 placed in the wells. A 1 mm hexagonally-packed imaging fiber contains approximately 20,600 individual optical fibers that have cores approximately 3.7 μm across (Part No. ET26 from Galileo Fibers). Typically, the cores of each fiber are hexagonally shaped as a result the starting preform; that is, during drawing the fiber does not usually change shape. In some cases, the shape can be circular, however.

In step 270, both the proximal and distal ends 212,214 of the fiber bundle 202 are successively polished on 12 μm, 9 μm, 3 μm, 1 μm, and 0.3 μm lapping films. Subsequently, the ends can be inspected for scratches on an atomic force microscope. In step 272, a representative etching is performed on the distal end 212 of the bundle 202. A solution of 0.2 grams $NH_4F$ (ammonium fluoride) with 600 μl distilled $H_2O$ and 100 μl of HF (hydrofluoric acid), 50% stock solution, may be used. The distal end 212 is etched in this solution for a specified time, preferably approximately 30 to 600 seconds, with about 80 seconds being preferred.

Upon removal from this solution, the bundle end is immediately placed in deionized water to stop any further etching in step 274. The fiber is then rinsed in running tap water. At this stage, sonication is preferably performed for several minutes to remove any salt products from the reaction. The fiber is then allowed to air dry.

The foregoing procedure produces wells by the anisotropic etching of the fiber cores 254 favorably with respect to the cladding 256 for each fiber of the bundle 202. The wells have approximately the diameter of the cores 254, 3.7 μm. This diameter is selected to be slightly larger than the diameters of the microspheres used, 3.1 μm, in the example. The preferential etching occurs because the pure silica of the cores 254 etches faster in the presence of hydrofluoric acid than the germanium-doped silica claddings 256.

The microspheres are then placed in the wells 250 in step 276 according to a number of different techniques. The placement of the microspheres may be accomplished by dripping a solution containing the desired randomly mixed subpopulations of the microspheres over the distal end 212, sonicating the bundle to settle the microspheres in the wells, and allowing the microsphere solvent to evaporate. Alternatively, the subpopulations could be added serially to the bundle end. Microspheres 10 may then be fixed into the wells 250 by using a dilute solution of sulfonated Nafion that is dripped over the end. Upon solvent evaporation, a thin film of Nafion was formed over the microspheres which holds them in place. This approach is compatible for fixing microspheres for pH indication that carry FITC functionality. The resulting array of fixed microspheres retains its pH sensitivity due to the permeability of the sulfonated Nafion to hydrogen ions. This approach, however, can not be employed generically as Nafion is impermeable to most water soluble species. A similar approach can be employed with different polymers. For example, solutions of polyethylene glycol, polyacrylamide, or polyhydroxymethyl methacrylate (polyHEMA) can be used in place of Nation, providing the requisite permeability to aqueous species.

An alternative fixation approach employs microsphere swelling to entrap each microsphere 10 in its corresponding microwell 250. In this approach, the microspheres are first distributed into the microwells 250 by sonicating the microspheres suspended in a non-swelling solvent in the presence of the microwell array on the distal end 212. After placement into the microwells, the microspheres are subsequently exposed to an aqueous buffer in which they swell, thereby physically entrapping them, analogous to muffins rising in a muffin tin.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

In a preferred embodiment, when non-covalent methods are used to associate the beads to the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differential affinity results in a competitive process, such that particles that will associate more tightly are selected. Preferably, the entire surface to be loaded' with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stiffing or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

One of the most common microsphere formations is tentagel, a styrene-polyethylene glycol co-polymer. These microspheres are unswollen in nonpolar solvents such as hexane and swell approximately 20-40% in volume upon exposure to a more polar or aqueous media. This approach is extremely desirable since it does not significantly compromise the diffusional or permeability properties of the microspheres themselves.

FIGS. 7A and 7B show polymer coated microspheres 12 in wells 250 after their initial placement and then after tapping and exposure to air pulses. FIGS. 7A and 7B illustrate that there is no appreciable loss of microspheres from the wells due to mechanical agitation even without a specific fixing technique. This effect is probably due to electrostatic forces between the microspheres and the optical fibers. These forces tend to bind the microspheres within the wells. Thus, in most environments, it may be unnecessary to use any chemical or mechanical fixation for the microspheres.

In a preferred embodiment, particularly when wells are used, a sonication step may be used to place beads in the wells.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

In addition, since the size of the array will be set by the number of unique optical signatures, it is possible to "reuse" a set of unique optical signatures to allow for a greater number of test sites. This may be done in several ways; for example, by using a positional coding scheme within an array; different sub-bundles may reuse the set of of optical signatures. Similarly, one embodiment utilizes bead size as a coding modality, thus allowing the reuse of the set of unique optical signatures for each bead size. Alternatively, sequential partial loading of arrays with beads can also allow the reuse of optical signatures.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of optical signatures; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, using its optical signature. The second sublibrary is then added, and the location of each optical signature is again determined. The signal in this case will comprise the "first" optical signature and the "second" optical signature; by comparing the two matrices the location of each bead in each sublibrary can be determined. Similarly, adding the third, fourth, etc. sublibraries sequentially will allow the array to be filled.

Thus, arrays are made of a large spectrum of chemical functionalities utilizing the compositions of invention comprising microspheres and substrates with discrete sites on a surface. Specifically, prior art sensors which can be adapted for use in the present invention include four broad classifications of microsphere sensors: 1) basic indicator chemistry sensors; 2) enzyme-based sensors; 3) immuno-based sensors (both of which are part of a broader general lass of protein sensors); and 4) geno-sensors.

In a preferred embodiment, the bioactive agents are used to detect chemical compounds. A large number of basic indicator sensors have been previously demonstrated. Examples include:

TABLE III

| TARGET ANALYTE | Bioactive agent | NOTES ($\lambda_{AB}/\lambda_{EM}$) |
|---|---|---|
| pH Sensors based on: | seminaphthofluoresceins | e.g., carboxyl-SNAFL |
| | seminaphthorhodafluors | e.g., carboxyl-SNARF |
| | 8-hydroxypyrene-1,3,6-trisulfonic acid | |
| | Fluorescein | |
| $CO_2$ Sensors based On: | seminaphthofluoresceins | e.g., carboxyl-SNAFL |
| | seminaphthorhodafluors | e.g., carbody-SNARF |
| | 8-hydroxypyrene-1,3,6-trisulfonic acid | |
| Metal Ions Sensors based on: | desferriozamine B | e.g., Fe |
| | cyclen derivative | e.g., Cu, Zn |
| | derivatized peptides | e.g., FITC-Gly-Gly-His, and FITC-Gly His, Cu, Zn |
| | fluorexon (calcine) | e.g., Ca, Mg, Cu, Pb, Ba |
| | calcine blue | e.g., Ca, Mg, Cu |
| | methyl calcine blue | e.g., Ca, Mg, Cu |
| | ortho-dianisidine tetracetic acid (ODTA) | e.g., Zn |
| | bis-salicylidene ethylenediamine (SED) | e.g., Al |
| | N-(6-methozy-8-quinolyl-p-toluenesulfonamine (TSQ) | e.g., Zn |
| | Indo-1 | e.g., Mn, Ni |
| | Fura-2 | e.g., Mn, Ni |
| | Magesium Green | e.g., Mg, Cd, Tb |
| $O_2$ | Siphenylisobenzofuran | 409/476 |
| | Methoxyvinyl pyrene | 352/401 |
| Nitrite | diaminonaphthalene | 340/377 |
| NO | Luminal | 355/411 |
| | dihydrohodamine | 289/none |
| $Ca^{2+}$ | Bis-fura | 340/380 |
| | Calcium Green | visible light/530 |
| | Fura-2 | 340/380 |
| | Indo-1 | 405/485 |
| | Fluo-3 | visible light/525 |
| | Rhod-2 | visible light/570 |
| $mg^{2+}$ | Mag-Fura-2 | 340/380 |
| | Mag-Fura-5 | 340/380 |
| | Mag-Indo-1 | 405/485 |
| | Magnesium Green | 475/530 |
| | Magnesium Orange | visible light/545 |
| $Zn^{2+}$ | Newport Green | 506/535 |
| TSQ | Methoxy-Quinobyl | 334/385 |
| $Cu^+$ | Phen Green | 492/517 |
| $Na^+$ | SBFI | 339/565 |
| | SBFO | 354/575 |
| | Sodium Green | 506/535 |
| $K^+$ | PBFI | 336/557 |
| $Cl^-$ | SPQ | 344/443 |
| | MQAE | 350/460 |

Each of the chemicals listed in Table III directly produces an optically interrogatable signal or a change in the optical signature, as is more fully outlined below, in the presence of the targeted analyte.

Enzyme-based microsphere sensors have also been demonstrated and could be manifest on microspheres. Examples include:

TABLE IV

| SENSOR TARGET | Bioactive agent |
|---|---|
| Glucose Sensor | glucose oxidase (enz.) + $O_2$-sensitive dye (see Table I) |
| Penicillin Sensor | penicillinase (enz.) + pH-sensitive dye (see Table I) |
| Urea Sensor | urease (enz.) + pH-sensitive dye (see Table I) |
| Acetylcholine Sensor | acetylcholinesterase (enz.) + pH-sensitive dye (see Table I) |

Generally, as more fully outlined above, the induced change in the optical signal due to the presence of the enzyme-sensitive chemical analyte occurs indirectly in this class of chemical functionalities. The microsphere-bound enzyme, e.g., glucose oxidase, decomposes the target analyte, e.g., glucose, consume a co-substrate, e.g., oxygen, or produce some by-product, e.g., hydrogen peroxide. An oxygen sensitive dye is then used to trigger the signal change. Thus, the product of the reaction is detected in a zone around the microsphere. That is, the product is not immobilized to the microsphere as is the enzyme, but rather the product is released from the microsphere-immobilized enzyme and detected in a region surrounding the microsphere.

Immuno-based microsphere sensors have been demonstrated for the detection for environmental pollutants such as pesticides, herbicides, PCB's and PAH's. Additionally, these sensors have also been used for diagnostics, such as bacterial (e.g., leprosy, cholera, lyme disease, and tuberculosis), viral (e.g., HIV, herpes simplex, cytomegalovirus), fungal (e.g., aspergillosis, candidiasis, cryptococcoses), Mycoplasmal (e.g., mycoplasmal pneumonia), Protozoal (e.g., amoebiasis, toxoplasmosis), Rickettsial (e.g., Rocky Mountain spotted fever), and pregnancy tests.

Microsphere genosensors may also be made (see the Examples). These are typically constructed by attaching a probe sequence to the microsphere surface chemistry, typically via an $NH_2$ group. A fluorescent dye molecule, e.g., fluorescein, is attached to the target sequence, which is in solution. The optically interrogatable signal change occurs with the binding of the target sequences to the microsphere. This produces a higher concentration of dye surrounding the microsphere than in the solution generally. A few demonstrated probe and target sequences, see Ferguson, J. A. et al. *Nature Biotechnology*, Vol. 14, December 1996, are listed below in Table V.

The present invention may be used with any or all of these types of sensors. As will be appreciated by those in the art, the type and composition of the sensor will vary widely, depending on the composition of the target analyte. That is, sensors may be made to detect nucleic acids, proteins (including enzyme sensors and immunosensors), lipids, carbohydrates, etc; similarly, these sensors may include bioactive agents that are nucleic acids, proteins, lipids, carbohydrates, etc. In addition, a single array sensor may contain different binding ligands for multiple types of analytes; for example, an array sensor for HIV may contain multiple, nucleic acid probes for direct detection of the viral genome, protein binding ligands for direct detection of the viral particle, immuno-components for the detection of anti-HIV antibodies, etc.

In addition to the beads and the substrate, the compositions of the invention may include other components, such as light sources, optical components such as lenses and filters, detectors, computer components for data analysis, etc.

The arrays of the present invention are constructed such that information about the identity of the bioactive agent is built into the array, such that the random deposition of the beads on the surface of the substrate can be "decoded" to allow identification of the bioactive agent at all positions. This may be done in a variety of ways.

In a preferred embodiment, the beads are loaded onto the substrate and then the array is decoded, prior to running the assay. This is done by detecting the optical signature associated with the bead at each site on the array. This may be done all at once, if unique optical signatures are used, or sequentially, as is generally outlined above for the "reuse" of sets of optical signatures. Alternatively, decoding may occur after the assay is run.

TABLE V

| PROBE SEQUENCES | TARGET SEQUENCES |
|---|---|
| B-glo(+) (segment of human B-globin) 5'-$NH_2$-$(CH_2)_8$-)TT TTT TTT TCA ACT TCA TCC ACG TTC ACC-3' (SEQ ID NO: 1) | B-glo(+)-CF 5'-Fluorescein-TC AAC GTG GAT GAA GTT C-3' 3' (SEQ ID NO: 2) |
| IFNG(interferon gamma 1) 5'-$NH_2$-$(CH_2)_8$-$T_{12}$-TGG CTT CTC TTG GCT GTT ACT-3' (SEQ ID NO: 3) | IFNG-CF 5-Fluorescein-AG TAA CAG CCA AGA GAA CCC AAA-3' (SEQ ID NO: 4) |
| IL2(interleukin-2) 5'-$NH_2$-$(CH_2)_8$-$T_{12}$-TA ACC GAA TCC CAA ACT CAC CAG-3' (SEQ ID NO: 5) | IL2-CF 5'-Fluorescein-CT GGT GAG TTT GGG ATT CTT GTA-3' (SEQ ID NO: 6) |
| IL4(interleukin-4) 5'$NH_2$-$(CH_2)_8$-$T_{12}$-CC AAC TGC TTC CCC CTC TGT-3' (SEQ ID NO: 7) | IL4-CF 5'Fluorescein-AC AGA GGG GGA AGC AGT TGG-3' (SEQ ID NO: 8) |
| IL6(interleukin-6) 5'$NH_2$-$(CH_2)_8$-$T_{12}$-GT TGG GTC AGG GGT GGT TAT T-3' (SEQ ID NO: 9) | IL6-CF 5'-Fluorescein-AA TAA CCA CCC CTG ACC CAA C-3' (SEQ ID NO: 10) |

It should be further noted that the genosensors can be based on the use of hybridization indicators as the labels. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up.

Once made and decoded if necessary, the compositions find use in a number of applications. Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, an intercalating dye (e.g., ethidium bromide) can be added subsequently to signal the presence of the bound target to the probe sequence. Upon binding of the target analyte to a bioactive agent, there is a new optical signal generated at that site, which then may be detected.

Alternatively, in some cases, as discussed above, the target analyte such as an enzyme generates a species (for example, a fluorescent product) that is either directly or indirectly detectable optically.

Furthermore, in some embodiments, a change in the optical signature may be the basis of the optical signal. For example, the interaction of some chemical target analytes with some fluorescent dyes on the beads may alter the optical signature, thus generating a different optical signal. For example, fluorophore derivatized receptors may be used in which the binding of the ligand alters the signal.

In a preferred embodiment, sensor redundancy is used. In this embodiment, a plurality of sensor elements, e.g. beads, comprising identical bioactive agents are used. That is, each subpopulation comprises a plurality of beads comprising identical bioactive agents (e.g. binding ligands). By using a number of identical sensor elements for a given array, the optical signal from each sensor element can be combined and any number of statistical analyses run, as outlined below. This can be done for a variety of reasons. For example, in time varying measurements, redundancy can significantly reduce the noise in the system. For non-time based measurements, redundancy can significantly increase the confidence of the data.

In a preferred embodiment, a plurality of identical sensor elements are used. As will be appreciated by those in the art, the number of identical sensor elements will vary with the application and use of the sensor array. In general, anywhere from 2 to thousands may be used, with from 2 to 100 being preferred, 2 to 50 being particularly preferred and from 5 to 20 being especially preferred. In general, preliminary results indicate that roughly 10 beads gives a sufficient advantage, although for some applications, more identical sensor elements can be used.

Once obtained, the optical response signals from a plurality of sensor beads within each bead subpopulation can be manipulated and analyzed in a wide variety of ways, including baseline adjustment, averaging, standard deviation analysis, distribution and duster analysis, confidence interval analysis, mean testing, etc.

In a preferred embodiment, the first manipulation of the optical response signals is an optional baseline adjustment. In a typical procedure, the standardized optical responses are adjusted to start at a value of 0.0 by subtracting the integer 1.0 from all data points. Doing this allows the baseline-loop data to remain at zero even when summed together and the random response signal noise is canceled out. When the sample is a vapor, the vapor pulse-loop temporal region, however, frequently exhibits a characteristic change in response, either positive, negative or neutral, prior to the vapor pulse and often requires a baseline adjustment to overcome noise associated with drift in the first few data points due to charge buildup in the CCD camera. If no drift is present, typically the baseline from the first data point for each bead sensor is subtracted from all the response data for the same bead. If drift is observed, the average baseline from the first ten data points for each bead sensor is subtracted from the all the response data for the same bead. By applying this baseline adjustment, when multiple bead responses are added together they can be amplified while the baseline remains at zero. Since all beads respond at the same time to the sample (e.g. the vapor pulse), they all see the pulse at the exact same time and there is no registering or adjusting needed for overlaying their responses. In addition, other types of baseline adjustment may be done, depending on the requirements and output of the system used.

Once the baseline has been adjusted, although in some embodiments this is not required, a number of possible statistical analyses may be run to generate known statistical parameters. Analyses based on redundancy are known and generally described in texts such as Freund and Walpole, Mathematical Statistics, Prentice Hall, Inc. New Jersey, 1980, hereby incorporated by reference in its entirety.

In a preferred embodiment, signal summing is done by simply adding the intensity values of all responses at each time point, generating a new temporal response comprised of the sum of all bead responses. These values can be baseline-adjusted or raw. As for all the analyses described herein, signal summing can be performed in real time or during post-data acquisition data reduction and analysis. In one embodiment, signal summing is performed with a commercial spreadsheet program (Excel, Microsoft, Redmond, Wash.) after optical response data is collected.

In a preferred embodiment, cumulative response data is generated by simply adding all data points in successive time intervals. This final column, comprised of the sum of all data points at a particular time interval, may then be compared or plotted with the individual bead responses to determine the extent of signal enhancement or improved signal-to-noise ratios.

In a preferred embodiment, the mean of the subpopulation (i.e. the plurality of identical beads) is determined, using the well known Equation 1:

$$\mu = \Sigma \frac{x_i}{n} \qquad \text{Equation 1}$$

In some embodiments, the subpopulation may be redefined to exclude some beads if necessary (for example for obvious outliers, as discussed below).

In a preferred embodiment, the standard deviation of the subpopulation can be determined, generally using Equation 2 (for the entire subpopulation) and Equation 3 (for less than the entire subpopulation):

$$\sigma = \sqrt{\frac{\Sigma(x_i - \mu)^2}{n}} \qquad \text{Equation 2}$$

$$s = \sqrt{\frac{\Sigma(x_i - \overline{x})^2}{n-1}} \quad \text{Equation 3}$$

As for the mean, the subpopulation may be redefined to exclude some beads if necessary (for example for obvious outliers, as discussed below).

In a preferred embodiment, statistical analyses are done to evaluate whether a particular data point has statistical validity within a subpopulation by using techniques including, but not limited to, t distribution and cluster analysis. This may be done to statistically discard outliers that may otherwise skew the result and increase the signal-to-noise ratio of any particular experiment. This may be done using Equation 4:

$$t = \frac{\overline{x} - \mu}{s/\sqrt{n}} \quad \text{Equation 4}$$

In a preferred embodiment, the quality of the data is evaluated using confidence intervals, as is known in the art. Confidence intervals can be used to facilitate more comprehensive data processing to measure the statistical validity of a result.

In a preferred embodiment, statistical parameters of a subpopulation of beads are used to do hypothesis testing. One application is tests concerning means, also called mean testing. In this application, statistical evaluation is done to determine whether two subpopulations are different. For example, one sample could be compared with another sample for each subpopulation within an array to determine if the variation is statistically significant.

In addition, mean testing can also be used to differentiate two different assays that share the same code. If the two assays give results that are statistically distinct from each other, then the subpopulations that share a common code can be distinguished from each other on the basis of the assay and the mean test, shown below in Equation 5:

$$z = \frac{\overline{x_1} - \overline{x_2}}{\sqrt{\frac{\sigma_1^2}{n_1} + \frac{\sigma_2^2}{n_2}}} \quad \text{Equation 5}$$

Furthermore, analyzing the distribution of individual members of a subpopulation of sensor elements may be done. For example, a subpopulation distribution can be evaluated to determine whether the distribution is binomial, Poisson, hypergeometric, etc.

In addition to the sensor redundancy, a preferred embodiment utilizes a plurality of sensor elements that are directed to a single target analyte but yet are not identical. For example, a single target nucleic acid analyte may have two or more sensor elements each comprising a different probe. This adds a level of confidence as non-specific binding interactions can be statistically minimized. When nucleic acid target analytes are to be evaluated, the redundant nucleic acid probes may be overlapping, adjacent, or spatially separated. However, it is preferred that two probes do not compete for a single binding site, so adjacent or separated probes are preferred. Similarly, when proteinaceous target analytes are to be evaluated, preferred embodiments utilize bioactive agent binding agents that bind to different parts of the target. For example, when antibodies (or antibody fragments) are used as bioactive agents for the binding of target proteins, preferred embodiments utilize antibodies to different epitopes.

In this embodiment, a plurality of different sensor elements may be used, with from about 2 to about 20 being preferred, and from about 2 to about 10 being especially preferred, and from 2 to about 5 being particularly preferred, including 2, 3, 4 or 5. However, as above, more may also be used, depending on the application.

As above, any number of statistical analyses may be run on the data from target redundant sensors.

One benefit of the sensor element summing (referred to herein as "bead summing" when beads are used), is the increase in sensitivity that can occur. Detection limits in the zeptomole range can be observed.

As will be appreciated by those in the art, in some embodiments, the presence or absence of the target analyte may be determined using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, the compositions are used to probe a sample solution for the presence or absence of a target analyte. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, dymidia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., *Science* 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$, with less than about $10^{-5}$ to $10^{-9} M^{-1}$ being preferred and less than about $10^{-7}$-$10^{-9}$ $M^{-1}$ being particularly preferred.

As described herein, in addition to the use of the sensors for detecting labeled analytes, the invention also provides for the detection of target analytes that affect enzymatic reactions. In general, this embodiment can be described as follows.

In one aspect the invention provides a method of detecting a target analyte in a sample. In one embodiment the target analyte is a molecule that modulates the activity of an enzyme. Alternatively, the target analyte is itself an enzyme. In addition the invention provides a reaction component that is immobilized at a discrete site on an array.

By "reaction component" is meant a molecule that affects a reaction, when contacted with other molecules. In a preferred embodiment the reaction is an enzymatic reaction, although it could also include chemical or binding reactions. By "affects" a reaction is meant to include but is not limited to inducing, activating, altering, for example slowing down or speeding up a reaction, or inhibiting a reaction.

By "immobilized" is meant to affix to a site on an array. In one embodiment immobilization is direct. That is, the reaction component is directly attached to the array. In an alternative embodiment, immobilization is indirect. In this embodiment, the reaction component is attached to the array through an intermediate moiety such as a microsphere. The reaction component is attached to the microsphere or array by any of the methods described herein.

When the target analyte is an enzyme, the reaction component modulates the activity of the enzyme. In a preferred embodiment the reaction component is a substrate for the enzyme, i.e. "enzyme substrate". When referring to enzyme substrates or substrates of an enzyme, the skilled artisan will recognize that this refers to a molecule that is converted by an enzyme into a product, as a result of an enzymatic reaction. In this embodiment, the array may include multiple discrete reaction components at different sites on the array. In one embodiment only some of the reaction components are substrates for the enzyme. Than is, a subset or subsets of reaction components are substrates for the enzyme.

Alternatively, the enzyme is immobilized at the discrete site, and a target analyte modulates the activity of the enzyme (the reaction component in this configuration). As is known in the art, molecules that modulate the activity of enzymes include but are not limited to substrates, co-factors, ligands, agonists, antagonists, inhibitors, and the like.

In one aspect, the invention provides a method for detecting the product of the enzymatic reaction as an indication of the presence of the enzyme and/or enzyme modulator. That is, upon enzyme activation, a product of the reaction is released from the array where it is detected. In a preferred embodiment, the product of the enzymatic reaction is detected upon its release from the enzyme in a zone around the discrete site where the enzyme and/or target analyte is located. That is, the product is detected in a zone surrounding the site on the array. By "around" or "surrounding" or grammatical equivalents herein is meant near the discrete site on the array. That is, the product is detected remote from or released from the discrete site. While it is appreciated that in some instances not all of the product will be released from the array, in a preferred embodiment substantially all of the product, once converted from the enzyme substrate, is released from the array. By "substantially all" is meant at least about 60 percent, preferably more than about 75 percent and most preferably more than about 85 percent.

As such, the product is detected not while immobilized, but rather while diffusing from the site. The product can be detected either directly or indirectly. That is, the released product either contains a detectable label or is otherwise directly detectable. Alternatively, the product can be detected indirectly. In this embodiment, the product binds to or associates with other molecules that produce or result in a detectable signal. In a preferred embodiment, the product is a substrate for a molecule such as an enzyme. When the product of the reaction is a substrate for a subsequent enzyme, the subsequent enzyme is a detection molecule as described herein.

Accordingly, in a preferred embodiment the invention provides a method of detecting a target analyte in a sample. The method includes providing an array as described herein. The array contains discrete sites to which reaction component(s) are attached. In some embodiments, the reaction component(s) are covalently attached. The array is contacted with the sample containing a target analyte and the product of an enzymatic reaction is detected in a region or zone around the site, as an indication of the presence of the target analyte.

In one embodiment the target analyte is an enzyme. As such, the samples contain at least one enzyme. In this embodiment, the reaction component is a substrate of the enzyme, or in an alternative embodiment, the reaction component is a co-factor. When the reaction component is not a substrate, the appropriate substrate is added to the array, for example in solution phase. In one embodiment each site contains a reaction component, although in another embodiment, each site includes at least two reaction components. That is, multiple reaction components are added in a single site.

In an alternative embodiment the target analyte is an enzyme substrate. As such, the reaction component is an enzyme. Alternatively, when the reaction component is an enzyme, the target analyte is an enzyme inhibitor.

The attachment of reaction components including enzymes or enzyme substrates to array sites, particularly beads, is outlined herein and will be appreciated by those in the art. In general, the use of flexible linkers is preferred, as this allows reaction components to interact with target analytes. However, for some types of attachment, linkers are not needed. Attachment proceeds on the basis of the composition of the array site (i.e. either the substrate or the bead, depending on which array system is used) and the composition of the enzyme. In a preferred embodiment, depending on the composition of the array site (e.g. the bead), it will contain chemical functional groups for subsequent attachment of other moieties. For example, beads comprising a variety of chemical functional groups such as amines are commercially available. Preferred functional groups for attachment are amino groups, carboxy groups, oxo groups and thiol groups, with amino groups being particularly preferred. Using these functional groups, the enzymes can be attached using functional groups on the enzymes. For example, enzymes containing amino groups can be attached to particles comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In one embodiment the reaction component is attached via a cleavable linker. By "cleavable linker" is meant a linker designed and intended to be specifically cleaved. Examples of cleavable linkers include photocleavable linkers, acid-cleavable linkers, and the like. Examples of cleavable linkers are outlined in more detail in U.S. Pat. No. 5,856,083, which is hereby expressly incorporated by reference.

In an alternative embodiment, at least one of the reaction components is non-cleavable. By "non-cleavable linker" is meant a linker that is not designed or intended to be specifically cleaved. That is, while the non-cleavable linkers are not resistant to all cleavage agents, the linker is not used so that the molecule to which it is attached can be released from the array. Thus, in contrast to the linkers as described in U.S. Pat. No. 5,856,063, the use of non-cleavable linkers to attach reaction components to the array results in a stable attachment of the reaction molecules.

In one embodiment the array comprises microspheres to which the reaction component is attached or reaction components are attached. Microspheres are distributed on the discrete sites on the array as described herein. However, other types of arrays are well known and can be used in this format; spotted, printed or photolithographic arrays are well known; see for example WO 95/25116; WO 95/35505; PCT US98/09163; U.S. Pat. Nos. 5,700,637; 5,807,522 and 5,445,934; and U.S. Ser. Nos. 08/851,203 09/187,289; and references cited within, all of which are expressly incorporated by reference. If beads are not used, preferred embodiments utilize a spotted array.

In some instances only one of the reactants (i.e. reaction components) is immobilized on the discrete site. As such, any other necessary reactants or co-factors are added to the immobilized reactant for example, in solution phase. The product of the reaction is released from the site into the area surrounding the site where it is detected by any of the detection methods as described herein.

In one embodiment, the target analyte is detected in a zone surrounding a discrete site on an array. That is, the target analyte is not immobilized or attached to the microsphere, but rather is detected in a region surrounding the discrete site.

In an alternative embodiment, the product of the reaction between the target analyte and the reaction component is detected in a zone surrounding a discrete site on an array. That is, following the enzymatic reaction, the product(s) is released from the immobilized reaction components. Thus, it is detected in a zone surrounding the site.

In one embodiment, when detecting a product in a zone surrounding a discrete site on an array, the reaction takes place in the presence of solutions and/or a matrix to slow down diffusion of the product from the site. That is, the reaction takes place in the presence of a diffusion retardant. In this respect, the product maintains an increased local concentration in the zone around the site for increased time. Solutions to diminish the diffusion of the product should not interfere the reaction between the reactants and include but are not limited to glycerol, polyethylene glycol, agarose, agar, polyacrylamide and other polymers. In a preferred embodiment the polymer is readily varied in its concentration so that the rate of diffusion of the product is adjusted as is necessary.

As one of skill in the art recognizes, enzymes that can be screened include but are not limited to polymerases, ligases, proteases including caspases, nucleotide cyclases, ribozymes, restriction endonucleases, transferases, lipases, and the like.

In one embodiment, the immobilized reactants correspond to known substrates of enzymes. As such, samples are screened for the presence of the particular enzyme by detecting a change in the respective immobilized substrate. In a preferred embodiment, a subpopulation of sites comprises discrete substrates for a plurality of enzymes. That is, a subpopulation contains substrates for a particular enzyme, yet the array may contain a population of microspheres that includes subpopulations that contain substrates for a number of enzymes. The array is contacted with a solution to be screened, for example, a tissue extract. A reaction between an enzyme and its respective substrate is detected as the product of the reaction is detected in the zone around the site containing the substrate molecule.

In an alternative embodiment a plurality of immobilized reactants are substrates for the same enzyme. That is, multiple sites on an array contain substrates for the same enzyme. In a preferred embodiment, the substrates are different. In one embodiment the substrates are different while remaining substrates for the same enzyme. For example, an array may contain multiple different oligonucleotides at different sites on an array. The oligonucleotides may contain unique or different sequences. However, all of the oligonucleotides are substrates for a polymerase or nuclease.

In one embodiment each microsphere contains multiple reaction components. That is, as is known in the art, certain enzymes require multiple substrates and/or cofactors. Accordingly, in this embodiment, a microsphere may contain a plurality of reaction components. The reaction components may include an enzyme, substrate, co-factor or other molecule that effects the reaction.

In one embodiment, the substrates are tagged or labeled such that the released product contains an identifier that is detectable, for example a fluorescent label. In a preferred embodiment, the substrates contain a fluorescent label that is quenched in the immobilized uncleaved substrate; however, upon cleavage, the released product containing the fluorescent label is unquenched and thus, emits a fluorescent signal in the zone surrounding the bead.

In an alternative embodiment, the released product is not directly detectable, but rather is indirectly detected by binding agents such as antibodies, or complementary nucleic acid probes. In this embodiment, the binding agents comprise the label.

In one embodiment the reaction product is a substrate for a detection molecule that may or may not be attached to the microspheres. By "detection molecule" is meant a molecule that reacts with the product from the first reaction to produce either directly or indirectly a detectable signal. When the detection molecule is not attached to the beads, it is added to the microsphere either prior to, simultaneously with or following the addition of the first mobile-phase reactant. When the detection molecule is immobilized to the microsphere it interacts with the reaction product following the first reaction. In this embodiment a microsphere may contain a reaction component and a detection molecule. Accordingly, in a preferred embodiment the product of the reaction with the reaction component is detected by the detection molecule.

In one embodiment the detection molecule is an enzyme that catalyzes a reaction, the product of which is directly detectable or as is well known in the art is converted to a substance that produces a detectable signal. As one of skill in the art appreciates, examples of detection molecules include but are not limited to β-galactosidase, firefly luciferase and the like.

In a preferred embodiment, particularly when secondary enzymes (detection molecules) are used in the reaction, the enzyme(s) may be attached, preferably through the use of flexible linkers, to the sites on the array, e.g. the beads, as described herein. For example, when pyrosequencing is done, one embodiment utilizes detection based on the generation of a chemiluminescent signal in the "zone" around the bead. Pyrosequencing is described in more detail in U.S. Ser. Nos. 60/130,089, 60/160,927, 09/513,362, 60/135,053, 09/425, 633, 09/535,854, 09/553,993 and 09/556,463, all of which are hereby expressly incorporated by reference in their entirety.

Pyrosequencing is an extension method that can be used to add one or more nucleotides to the 3'-terminus of an oligonucleotide. Pyrosequencing relies on the detection of a reaction product, PPi, produced during the addition of an NTP to a growing oligonucleotide chain, rather than on a label attached to the nucleotide. One molecule of PPi is produced per dNTP added to the extension primer. Accordingly, by running sequential reactions with each of the nucleotides, and monitoring the reaction products, the identity of the added base is determined.

The release of pyrophosphate (PPi) during the DNA polymerase reaction can be quantitatively measured by many different methods and a number of enzymatic methods have been described; see Reeves et al., *Anal. Biochem.* 28:282 (1969); Guillory et al., *Anal. Biochem.* 39:170 (1971); Johnson et al., *Anal. Biochem.* 15:273 (1968); Cook et al., *Anal. Biochem.* 91:557 (1978); Drake et al., *Anal. Biochem.* 94:117 (1979); WO93/23564; WO98/28440; WO98/13523; Nyren et al., *Anal. Biochem.* 151:504 (1985); all of which are incorporated by reference. The latter method allows continuous monitoring of PPi and has been termed ELIDA (Enzymatic Luminometric Inorganic Pyrophosphate Detection Assay). A preferred embodiment utilizes any method which can result in the generation of an optical signal, with preferred embodiments utilizing the generation of a chemiluminescent or fluorescent signal.

A preferred method monitors the creation of PPi by the conversion of PPi to ATP by the enzyme sulfurylase, and the subsequent production of visible light by firefly luciferase (see Ronaghi et al., *Science* 281:363 (1998), incorporated by reference). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

Accordingly, a preferred embodiment of the methods of the invention is as follows. A substrate comprising microspheres containing the target sequences and extension primers, forming hybridization complexes, is dipped or contacted with a reaction chamber or well comprising a single type of dNTP, an extension enzyme, and the reagents and enzymes necessary to detect PPi. If the dNTP is complementary to the base of the target portion of the target sequence adjacent to the extension primer, the dNTP is added, releasing PPi and generating detectable light in a region or zone around the microsphere, which is detected as generally described in U.S. Ser. Nos. 09/151,877 and 09/189,543, and PCT US98/09163, all of which are hereby incorporated by reference. If the dNTP is not complementary, no detectable signal results. The substrate is then contacted with a second reaction chamber comprising a different dNTP and the additional components of the assay. This process is repeated if the identity of a base at a second detection position is desirable.

In a preferred embodiment, one or more internal control sequences are used. That is, at least one microsphere in the array comprises a known sequence that can be used to verify that the reactions are proceeding correctly. In a preferred embodiment, at least four control sequences are used, each of which has a different nucleotide at each position: the first control sequence will have an adenosine at position 1, the second will have a cytosine, the third a guanosine, and the fourth a thymidine, thus ensuring that at least one control sequence is "lighting up" at each step to serve as an internal control.

The pyrosequencing systems may be configured in a variety of ways; for example, the target sequence may be attached to the bead in a variety of ways, including direct attachment of the target sequence; the use of a capture probe with a separate extension probe; the use of a capture extender probe, a capture probe and a separate extension probe; the use of adapter sequences in the target sequence with capture and extension probes; and the use of a capture probe that also serves as the extension probe.

One additional benefit of pyrosequencing for genotyping purposes is that since the reaction does not rely on the incorporation of labels into a growing chain, the unreacted extension primers need not be removed.

Moreover, when the secondary enzymes required to generate the signal are attached to the microspheres, an increased concentration of the required enzymes is obtained in the immediate vicinity of the reaction on the microspheres. This allows for the use of less enzyme and results in faster reaction rates for detection. Thus, preferred embodiments utilize the attachment, preferably covalently (although as will be appreciated by those in the art, other attachment mechanisms may be used), of the secondary enzymes used to generate the signal.

As outlined above for pyrosequencing, the generation and detection of PPi results in a signal in a zone around a discrete site on an array. Accordingly, in one embodiment, the method of the invention finds use in detecting any enzyme that produces PPi. Enzymes that produce PPi include, but are not limited to nucleotide cyclases, nucleotide polymerases and the like.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Enzyme-Based Sensor

Subpopulation A
Bioactive agent: Alkaline phosphatase
Target substrate: fluorescein diphosphate (FDP)
Reported dye ratio: 1:1 ratio of DilC:TRC, where DilC is 1,1',3,3,3',3'-hexamethyl-indodicarbocyanine iodide and TRC is Texas Red cadaverine A range of ratios of light intensities are selected that are representative of the optical signature for the dye ratio of the subpopulation based on the quantum yield of the two dyes. The optical signature for this subpopulation is:
  DilC λ intensity-ave.DilC background=0.847±0.23
  TRC λ intensity-ave.TRC background
Subpopulation B
Bioactive agent: B-Galactosidase;
Target substrate=fluorescein di-B-galactopyranoside (FDG)
Reporter dye ratio: 10:1 ratio of DilC:TRC which translates to an optical signature of:
  DilC λ intensity-ave.DilC background=4.456±1.27
  TRC λ intensity-ave.TRC background
Subpopulation C
Bioactive agent: B-glucuronidase
Target substrate=fluorescein di-B-D-glucuronide (FDGicu).
Reporter dye ratio: 1:10 ratio of DilC:TRC, which translates to an optical signature of:
  DilC A intensity-ave. DilC background=0.2136±0.03
  TRC A intensity-ave. TRC background When the microsphere populations are in the presence of one or more of the substrates, the respective enzymes on the microspheres catalyze the breakdown of the substrates producing fluorescein which is fluorescent, emitting light at 530 nanometers when excited at 490 nm. The production of fluorescein localized to particular beads is then monitored. In this approach, the localization of fluorescein around the microspheres is increased by using a substrate solution of 90% glycerol and 10% substrate. The glycerol inhibits the generated fluorescein from diffusing away from the microsphere reaction sites.

During the experiment, images in the encoded wavelengths are first taken. Since both DilC and TRC are excited at 577 nm. Each microsphere's emissions at 670 nm, indicative of the presence of DilC and 610 nm indicative of the presence of TRC were recorded using a 595 nm dichroic and an acquisition time of 5 seconds for the CCD 236. Next, the distal end 212 of the fiber bundle is placed in a buffer and another image taken while illuminating the beams with 490 nm light. Emissions in the 530 nm fluorescein wavelengths were recorded with a 505 nm dichroic. In this case, a CCD acquisition time of one second was used. This process provides a background normalizing image. The buffer was removed and the fiber allowed to dry to avoid substrate solution dilution.

The substrate solution is then introduced and CCD images acquired every 30 seconds to a minute for 30 minutes While illuminating the microspheres with 490 nm light and collecting emissions in the 530 nm range. Fiber is then placed back in the buffer solution and another background image captured. Those beads that generate a signal indicative of fluorescein production are decoded. Depending in the ratio of the intensity of light from the two reporter dyes, DilC:TRC, the bioactive agent of the optically active beads may be decoded according to the following table.

| | |
|---|---|
| 0.617-1.08 | alkaline phosphatase bead |
| 3.188-5.725 | β-galactosidase bead |
| 0.183-0.243 | β-glucunonidase bead |

This process is then repeated for the remaining two substrates.

FIGS. 8A-8C are images generated by the CCD 236 when the bead populations are exposed to fluorescein diphosphate. FIG. 8A illustrates the signals from the alkaline phosphatase microspheres when excited at 490 nm and recording emissions at 530 nm, emissions at this wavelength being indicative of fluorescein production. FIG. 8B shows the image captured by the CCD when the microspheres are excited at 577 nm and emissions at 670 nm are recorded. This wavelength is an encoding wavelength indicative of the concentration of Di1C on the microspheres. Finally, FIG. 8C shows the image when the microspheres are excited with 577 nm light and emissions in the 610 nm range are recorded being indicative of the concentration of TRC in the microspheres.

In a similar vein, FIGS. 9A and 9B are images when the microspheres are exposed to fluorescein β-d-galactosidase. FIG. 9A shows emissions at 530 nm indicative of the fluorescein production; and FIG. 9B shows light emitted at the 670 nm range indicative of the presence of Di1C.

These micrographs, FIGS. 8A-8C and 9A-9B illustrate that fluorescein production around the microspheres may be detected as an optical signature change indicative of reactions involving the bioactive agent of the microspheres. The micrographs also illustrate that the optical signatures may be decoded to determine the chemical functionalities on each microsphere.

Immunosensor

Three separate subpopulations of beads were used. In subpopulation A, xrabbit antibodies (Ab) were affixed to the surface of the microspheres; in subpopulation B, xgoat antibodies were affixed to the microspheres; and in subpopulation C, xmouse antibodies were affixed to the microspheres. These three separate subpopulations were identified using a Di1C: TRC encoding ratio similar to that in the previously described experiment.

For the first step of the experiment, images at the encoded wavelengths were captured using 577 nm excitation and looking for emissions at 610 and 670 nm. After this decoding, the fiber was placed in a buffer and an image taken at 530 nm with 490 nm excitation. This provided a background normalizing signal at the fluorescein emission wavelength. Next, the fiber was placed in rabbit IgG antigen (Ag) which is fluorescein labeled. Images were then captured every few minutes at the 530 nm emission wavelength for fluorescein. FIGS. 10A and 10B are micrographs showing the image captured by the CCD prior to and subsequent to exposure to a rabbit antigen, which dearly show reaction of the selected micropheres within the population.

Note, if the fluorescein background from the antigen solution is too high to see the antibody-antigen signal, the fiber bundle may be placed in a buffer. This removes the background florescence leaving only the Ab-Ag signal.

While this invention has been particularly shown and described with references to preferred embodiments thereof, it will be understood by those skilled in the art that various changes in form and details may be made therein without departing from the spirit and scope of the invention as defined by the appended claims.

---

We claim:

1. An assay kit comprising:
an array substrate having a surface comprising a plurality of wells, wherein the wells are at a density of at least 10,000 sites per 1 mm$^2$; and
a population of beads, wherein beads of said population are sized to fit within said wells and are functionalized with a nucleic acid, and wherein each well is dimensioned so as to accommodate not more than one bead of said population of beads, wherein the substrate is a fiber optic bundle.

2. An assay kit comprising:
an array substrate having a surface comprising a plurality of wells, wherein the wells are at a density of at least 10,000 sites per 1 mm$^2$; and
a population of beads, wherein beads of said population are sized to fit within said wells and are functionalized with a nucleic acid, and wherein each well is dimensioned so as to accommodate not more than one bead of said population of beads, wherein the wells are chemically altered.

3. The assay kit of claim 2, wherein the wells comprise sites selected from the group consisting of chemically functionalized sites, electrostatically altered sites, hydrophobically functionalized sites, hydrophilically functionalized sites, and spots of adhesive.

4. The assay kit of claim 2, wherein the wells are hydrophilic.

5. The assay kit of claim 2, wherein the wells are hydrophobic.

6. The assay kit of claim 2, wherein the wells comprise charged chemical groups.

7. The assay kit of claim 2, wherein the wells comprise a chemical functional group selected from the group consisting of an amino group, a carboxy group, an oxo group, and a thiol group.

8. The assay kit of claim 2, wherein beads of said population comprise one or more optical encoding parameters.

9. The assay kit of claim 2, wherein the substrate is selected from the group consisting of glass and plastic.

10. The assay kit of claim 2, wherein the substrate is planar.

11. The assay kit of claim 2, wherein the wells are at a density of at least 20,000 sites per 1 mm$^2$.

12. The assay kit of claim 2, wherein the wells are at a density of at least 100,000 sites per 1 mm$^2$.

* * * * *

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: Probe

<400> SEQUENCE: 1 ttttttttc aacttcatcc acgttcacc                                    29

<210> SEQ ID NO 2
<211> LENGTH: 18
<212> TYPE: DNA
<213> ORGANISM: Artificial Sequence
<220> FEATURE:
<223> OTHER INFORMATION: Probe

<400> SEQUENCE: 2
tcaacgtgga tgaagttc                                               18

<210> SEQ ID NO 3
<211> LENGTH: 33
<212> TYPE: DNA
<213> ORGANISM: Artificial Sequence
<220> FEATURE:
<223> OTHER INFORMATION: Probe

<400> SEQUENCE: 3
tttttttttt tttggcttct cttggctgtt act                              33

<210> SEQ ID NO 4
<211> LENGTH: 23
<212> TYPE: DNA
```

```
<213> ORGANISM: Artificial Sequence
<220> FEATURE:
<223> OTHER INFORMATION: Probe

<400> SEQUENCE: 4
agtaacagcc aagagaaccc aaa                                              23

<210> SEQ ID NO 5
<211> LENGTH: 35
<212> TYPE: DNA
<213> ORGANISM: Artificial Sequence
<220> FEATURE:
<223> OTHER INFORMATION: Probe

<400> SEQUENCE: 5
tttttttttt tttaaccgaa tcccaaactc accag                                 35

<210> SEQ ID NO 6
<211> LENGTH: 23
<212> TYPE: DNA
<213> ORGANISM: Artificial Sequence
<220> FEATURE:
<223> OTHER INFORMATION: Probe

<400> SEQUENCE: 6
ctggtgagtt tgggattctt gta                                              23

<210> SEQ ID NO 7
<211> LENGTH: 32
<212> TYPE: DNA
<213> ORGANISM: Artificial Sequence
<220> FEATURE:
<223> OTHER INFORMATION: Probe

<400> SEQUENCE: 7
tttttttttt ttccaactgc ttcccctct gt                                     32

<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
acagaggggg aagcagttgg                                                  20

<210> SEQ ID NO 9
<211> LENGTH: 33
<212> TYPE: DNA
<213> ORGANISM: Artificial Sequence
<220> FEATURE:
<223> OTHER INFORMATION: Probe

<400> SEQUENCE: 9
tttttttttt ttgttgggtc agggtggtt att                                    33

<210> SEQ ID NO 10
<211> LENGTH: 21
<212> TYPE: DNA
<213> ORGANISM: Artificial Sequence
<220> FEATURE:
<223> OTHER INFORMATION: Probe
```

```
<400> SEQUENCE: 10
aataaccacc cctgacccaa c                                              21
```